United States Patent [19]
Packett et al.

[11] Patent Number: 5,892,127
[45] Date of Patent: Apr. 6, 1999

[54] PROCESSES FOR PRODUCING 1,6-HEXANEDIALS AND DERIVATIVES

[75] Inventors: Diane Lee Packett, South Charleston; John Robert Briggs, Charleston; David Robert Bryant, South Charleston; Ailene Gardner Phillips, Charleston, all of W. Va.

[73] Assignee: Union Carbide Chemicals & Plastics Technology Corporation, Danbury, Conn.

[21] Appl. No.: 842,665

[22] Filed: Apr. 15, 1997

Related U.S. Application Data

[60] Provisional application Nos. 60/015,942, 60/015,946, 60/015,952, 60/016,128, 60/016,162, 60/016,175, 60/016,179, 60/016,267, 60/016,279, 60/016,282 and 60/016,335 all filed Apr. 24, 1996.

[51] Int. Cl.$^6$ .................................................. C07C 45/50
[52] U.S. Cl. .......................................... 568/454; 568/451
[58] Field of Search ...................... 568/454, 451

[56] References Cited

U.S. PATENT DOCUMENTS

| | | | |
|---|---|---|---|
| 2,912,464 | 11/1959 | Hess et al. | 260/604 |
| 3,947,503 | 3/1976 | Kummer | 260/635 |
| 4,248,802 | 2/1981 | Kuntz | 568/454 |
| 4,507,508 | 3/1985 | Hayden et al. | 568/487 |
| 4,769,498 | 9/1988 | Billig et al. | 568/454 |
| 4,808,756 | 2/1989 | Tikitoh et al. | 568/454 |
| 4,835,299 | 5/1989 | Maher | 558/85 |
| 5,312,996 | 5/1994 | Packett | 568/454 |

FOREIGN PATENT DOCUMENTS

| | | |
|---|---|---|
| 0033554 | 8/1981 | European Pat. Off. . |
| 0094748 | 11/1983 | European Pat. Off. . |
| 0309056 | 3/1989 | European Pat. Off. . |
| 0407687 | 1/1991 | European Pat. Off. . |

OTHER PUBLICATIONS

B. Fell, Cobalt Carbonyl and Rhodium Carbonyl Catalyst Systems in Hydroformylation of 1,3–Dienes, 99, 452–8 (1975).

B. Fell, et al., Dialdehydes by Hydroformylation of Conjugated Dienes, Tetrahedron Letters No. 32, pp. 2721–2723 (1969).

R. Kummer, et al., Diols by Hydroformylation of Conjugated Dienes, Proc Symp. Rhodium Homegeneous Catal., pp. 87–93 (1978).

I. Wender, et al., Chemistry of the Oxo and Related Reactions. II. Hydrogenation, Contribution from the Laboratory of Organic Chemistry of the University of Wisconsin, pp. 4375–4378 (1950).

H. Adkins, et al., Hydroformylation of Conjugated Dienes, pp. 980–987 (1952).

*Primary Examiner*—Gary Geist
*Assistant Examiner*—Sreeni Padmanabhan
*Attorney, Agent, or Firm*—Gerald L. Coon

[57] ABSTRACT

This invention relates in part to processes for selectively producing one or more substituted or unsubstituted 1,6-hexanedials, e.g., adipaldehyde, which comprise: (a) subjecting one or more substituted or unsubstituted alkadienes, e.g., butadiene, or a mixture comprising one or more substituted or unsubstituted alkadienes to hydroformylation in the presence of a hydroformylation catalyst, e.g., a metal-organophosphorus ligand complex catalyst, and at an alkadiene partial pressure and/or a carbon monoxide partial pressure sufficient to selectively produce one or more substituted or unsubstituted pentenals or a reaction mixture comprising one or more substituted or unsubstituted pentenals; and (b) subjecting said one or more substituted or unsubstituted pentenals or said reaction mixture comprising one or more substituted or unsubstituted pentenals to hydroformylation in the presence of a hydroformylation catalyst, e.g., a metal-organophosphorus ligand complex catalyst, to selectively produce said one or more substituted or unsubstituted 1,6-hexanedials. The substituted or unsubstituted 1,6-hexanedials produced by the processes of this invention can undergo further reaction(s) to afford desired derivatives thereof, e.g., epsilon caprolactone. This invention also relates in part to reaction mixtures containing one or more substituted or unsubstituted 1,6-hexanedials as principal product(s) of reaction.

31 Claims, No Drawings

PROCESSES FOR PRODUCING 1,6-HEXANEDIALS AND DERIVATIVES

This application claims the benefit of provisional U.S. patent application Ser. Nos. 60/016279, 60/015946, 60/015942, 60/016267, 60/015952, 60/016162, 60/016179, 60/016,128, 60/016175, 60/016282 and 60/016335, all filed Apr. 24, 1996, and all of the disclosures of which are incorporated herein by reference.

BRIEF SUMMARY OF THE INVENTION

1. Technical Field

This invention relates in part to processes for selectively producing one or more substituted or unsubstituted 1,6-hexanedials or reaction mixtures comprising one or more substituted or unsubstituted 1,6-hexanedials. This invention also relates in part to reaction mixtures containing one or more substituted or unsubstituted 1,6-hexanedials as principal reaction product or products.

2. Background of the Invention

Adipaldehyde is a valuable intermediate which is useful, for example, in the production of adipic acid by oxidation and in the production of 1,6-hexanediol by hydrogenation. Adipic acid and 1,6-hexanediol are also produced from other intermediates (e.g., adipic acid is also produced from cyclohexanone by oxidation). Adipaldehyde itself is produced by circuitous and/or expensive routes such as by the ozonolysis of cyclohexane.

The processes currently used to produce adipaldehyde, adipic acid and 1,6-hexanediol have various disadvantages. For example, the oxidation reactions may involve the use of nitric acid which can produce nitrous oxide which is an ozone scavenger and which, therefore, may contribute to the greenhouse effect. Moreover, starting materials currently used to produce adipaldehyde, adipic acid and 1,6-hexanediol are relatively expensive. In addition, the selectivity to adipaldehyde in prior butadiene hydroformylation processes has been low. Accordingly, it would be desirable to produce adipaldehyde from a relatively inexpensive starting material (e.g., pentenal) and by a process (e.g., hydroformylation) which does not have the disadvantages of prior art processes.

3. Disclosure of the Invention

This invention relates to processes for selectively producing one or more substituted or unsubstituted 1,6-hexanedials, e.g., adipaldehyde, which comprise: (a) subjecting one or more substituted or unsubstituted alkadienes, e.g., butadiene, or a mixture comprising one or more substituted or unsubstituted alkadienes to hydroformylation in the presence of a hydroformylation catalyst, e.g., a metal-organophosphorus ligand complex catalyst, and at an alkadiene partial pressure and/or a carbon monoxide partial pressure sufficient to selectively produce one or more substituted or unsubstituted pentenals or a reaction mixture comprising one or more substituted or unsubstituted pentenals; and (b) subjecting said one or more substituted or unsubstituted pentenals or said reaction mixture comprising one or more substituted or unsubstituted pentenals to hydroformylation in the presence of a hydroformylation catalyst, e.g., a metal-organophosphorus ligand complex catalyst, to selectively produce said one or more substituted or unsubstituted 1,6-hexanedials. In an embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in steps (a) and (b) may be the same or different and the hydroformylation catalysts in steps (a) and (b) may be the same or different.

This invention also relates to processes for selectively producing one or more substituted or unsubstituted 1,6-hexanedials, e.g., adipaldehyde, which comprise: (a) reacting one or more substituted or unsubstituted alkadienes, e.g., butadiene, or a mixture comprising one or more substituted or unsubstituted alkadienes with hydrogen and carbon monoxide in the presence of a catalytic amount of a metal-ligand complex catalyst and at an alkadiene partial pressure and/or a carbon monoxide partial pressure sufficient to selectively produce one or more substituted or unsubstituted pentenals or a reaction mixture comprising one or more substituted or unsubstituted pentenals; and (b) reacting said one or more substituted or unsubstituted pentenals or said reaction mixture comprising one or more substituted or unsubstituted pentenals with hydrogen and carbon monoxide in the presence of a catalytic amount of a metal-ligand complex catalyst to selectively produce said one or more substituted or unsubstituted 1,6-hexanedials. In an embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in steps (a) and (b) may be the same or different and the hydroformylation catalysts in steps (a) and (b) may be the same or different.

This invention further relates to a process for producing a batchwise or continuously generated reaction mixture comprising:

(1) one or more substituted or unsubstituted 1,6-hexanedials, e.g., adipaldehyde;

(2) one or more substituted or unsubstituted pentenals, e.g., cis-2-pentenal, trans-2-pentenal, cis-3-pentenal, trans-3-pentenal and/or 4-pentenal;

(3) one or more substituted 1,5-pentanedials, e.g., 2-methylglutaraldehyde;

(4) one or more substituted 1,4-butanedials, e.g., 2,3-dimethylsuccinaldehyde and 2-ethylsuccinaldehyde;

(5) optionally valeraldehyde; and (6) one or more substituted or unsubstituted alkadienes, e.g., butadiene;

wherein the weight ratio of component (1) to component (2) is greater than about 0.01, preferably greater than about 0.1; the weight ratio of component (1) to the sum of components (2), (3), (4) and (5) is greater than about 0.1, preferably greater than about 0.25; and the weight ratio of component (6) to the sum of components (1), (2), (3), (4) and (5) is about 0 to about 100, preferably about 0.001 to about 50;

which process comprises: (a) subjecting one or more substituted or unsubstituted alkadienes, e.g., butadiene, or a mixture comprising one or more substituted or unsubstituted alkadienes to hydroformylation in the presence of a hydroformylation catalyst, e.g., a metal-organophosphorus ligand complex catalyst, and at an alkadiene partial pressure and/or a carbon monoxide partial pressure sufficient to selectively produce one or more substituted or unsubstituted pentenals or a reaction mixture comprising one or more substituted or unsubstituted pentenals; and (b) subjecting said one or more substituted or unsubstituted pentenals or said reaction mixture comprising one or more substituted or unsubstituted pentenals to hydroformylation in the presence of a hydroformylation catalyst, e.g., a metal-organophosphorus ligand complex catalyst, to produce said batchwise or continuously generated reaction mixture. In an embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in steps (a) and (b) may be the same or different and the hydroformylation catalysts in steps (a) and (b) may be the same or different.

This invention yet further relates to a process for producing a batchwise or continuously generated reaction mixture comprising:

(1) one or more substituted or unsubstituted 1,6-hexanedials, e.g., adipaldehyde;

(2) one or more substituted or unsubstituted pentenals, e.g., cis-2-pentenal, trans-2-pentenal, cis-3-pentenal, trans-3-pentenal and/or 4-pentenal;

(3) one or more substituted 1,5-pentanedials, e.g., 2-methylglutaraldehyde;

(4) one or more substituted 1,4-butanedials, e.g., 2,3-dimethylsuccinaldehyde and 2-ethylsuccinaldehyde;

(5) optionally valeraldehyde; and (6) one or more substituted or unsubstituted alkadienes, e.g., butadiene;

wherein the weight ratio of component (1) to component (2) is greater than about 0.01, preferably greater than about 0.1; the weight ratio of component (1) to the sum of components (2), (3), (4) and (5) is greater than about 0.1, preferably greater than about 0.25; and the weight ratio of component (6) to the sum of components (1), (2), (3), (4) and (5) is about 0 to about 100, preferably about 0.001 to about 50; which process comprises: (a) reacting one or more substituted or unsubstituted alkadienes, e.g., butadiene, or a mixture comprising one or more substituted or unsubstituted alkadienes with hydrogen and carbon monoxide in the presence of a catalytic amount of a metal-ligand complex catalyst and at an alkadiene partial pressure and/or a carbon monoxide partial pressure sufficient to selectively produce one or more substituted or unsubstituted pentenals or a reaction mixture comprising one or more substituted or unsubstituted pentenals; and (b) reacting said one or more substituted or unsubstituted pentenals or said reaction mixture comprising one or more substituted or unsubstituted pentenals with hydrogen and carbon monoxide in the presence of a catalytic amount of a metal-ligand complex catalyst to produce said batchwise or continuously generated reaction mixture. In an embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in steps (a) and (b) may be the same or different and the hydroformylation catalysts in steps (a) and (b) may be the same or different.

This invention also relates to a process for producing a reaction mixture comprising one or more substituted or unsubstituted 1,6-hexanedials, e.g., adipaldehyde, which process comprises: (a) subjecting one or more substituted or unsubstituted alkadienes, e.g., butadiene, or a mixture comprising one or more substituted or unsubstituted alkadienes to hydroformylation in the presence of a hydroformylation catalyst, e.g., a metal-organophosphorus ligand complex catalyst, and at an alkadiene partial pressure and/or a carbon monoxide partial pressure sufficient to selectively produce one or more substituted or unsubstituted pentenals or a reaction mixture comprising one or more substituted or unsubstituted pentenals; and (b) subjecting said one or more substituted or unsubstituted pentenals or said reaction mixture comprising one or more substituted or unsubstituted pentenals to hydroformylation in the presence of a hydroformylation catalyst, e.g., a metal-organophosphorus ligand complex catalyst, to produce said reaction mixture comprising one or more substituted or unsubstituted 1,6-hexanedials. In an embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in steps (a) and (b) may be the same or different and the hydroformylation catalysts in steps (a) and (b) may be the same or different.

This invention further relates to a process for producing a reaction mixture comprising one or more substituted or unsubstituted 1,6-hexanedials, e.g., adipaldehyde, which process comprises: (a) reacting one or more substituted or unsubstituted alkadienes, e.g., butadiene, or a mixture comprising one or more substituted or unsubstituted alkadienes with hydrogen and carbon monoxide in the presence of a catalytic amount of a metal-ligand complex catalyst and at an alkadiene partial pressure and/or a carbon monoxide partial pressure sufficient to selectively produce one or more substituted or unsubstituted pentenals or a reaction mixture comprising one or more substituted or unsubstituted pentenals; and (b) reacting said one or more substituted or unsubstituted pentenals or said reaction mixture comprising one or more substituted or unsubstituted pentenals with hydrogen and carbon monoxide in the presence of a catalytic amount of a metal-ligand complex catalyst to produce said reaction mixture comprising one or more substituted or unsubstituted 1,6-hexanedials. In an embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in steps (a) and (b) may be the same or different and the hydroformylation catalysts in steps (a) and (b) may be the same or different.

The processes of this invention can achieve higher selectivities of alkadienes to 1,6-hexanedials than have been achieved in prior art processes. Thus selectivities of alkadienes to 1,6-hexanedials of at least 10% by weight and up to 85% by weight or greater may be achieved by the processes of this invention.

This invention yet further relates to a batchwise or continuously generated reaction mixture comprising:

(1) one or more substituted or unsubstituted 1,6-hexanedials, e.g., adipaldehyde;

(2) one or more substituted or unsubstituted pentenals, e.g., cis-2-pentenal, trans-2-pentenal, cis-3-pentenal, trans-3-pentenal and/or 4-pentenal;

(3) one or more substituted 1,5-pentanedials, e.g., 2-methylglutaraldehyde;

(4) one or more substituted 1,4-butanedials, e.g., 2,3-dimethylsuccinaldehyde and 2-ethylsuccinaldehyde;

(5) optionally valeraldehyde; and (6) one or more substituted or unsubstituted alkadienes, e.g., butadiene;

wherein the weight ratio of component (1) to component (2) is greater than about 0.01, preferably greater than about 0.1;

the weight ratio of component (1) to the sum of components (2), (3), (4) and (5) is greater than about 0.1, preferably greater than about 0.25; and the weight ratio of component (6) to the sum of components (1), (2), (3), (4) and (5) is about 0 to about 100, preferably about 0.001 to about 50.

This invention also relates to a reaction mixture comprising one or more substituted or unsubstituted 1,6-hexanedials, e.g., adipaldehyde, in which said reaction mixture is prepared by a process which comprises: (a) subjecting one or more substituted or unsubstituted alkadienes, e.g., butadiene, or a mixture comprising one or more substituted or unsubstituted alkadienes to hydroformylation in the presence of a hydroformylation catalyst, e.g., a metal-organophosphorus ligand complex catalyst, and at an alkadiene partial pressure and/or a carbon monoxide partial pressure sufficient to selectively produce one or more substituted or unsubstituted pentenals or a reaction mixture comprising one or more substituted or unsubstituted pentenals; and (b) subjecting said one or more substituted or unsubstituted pentenals or said reaction mixture comprising one or more substituted or unsubstituted pentenals to hydroformylation in the presence of a hydroformylation catalyst, e.g., a metal-organophosphorus ligand complex catalyst, to produce said reaction mixture comprising one or more substituted or unsubstituted 1,6-hexanedials. In an embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in steps (a) and (b) may be the same or different and the hydroformylation catalysts in steps (a) and (b) may be the same or different.

This invention further relates to a reaction mixture comprising one or more substituted or unsubstituted 1,6-hexanedials, e.g., adipaldehyde, in which said reaction mixture is prepared by a process which comprises: (a) reacting one or more substituted or unsubstituted alkadienes, e.g., butadiene, or a mixture comprising one or more substituted or unsubstituted alkadienes with hydrogen and carbon monoxide in the presence of a catalytic amount of a metal-ligand complex catalyst and at an alkadiene partial pressure and/or a carbon monoxide partial pressure sufficient to selectively produce one or more substituted or unsubstituted pentenals or a reaction mixture comprising one or more substituted or unsubstituted pentenals; and (b) reacting said one or more substituted or unsubstituted pentenals or said reaction mixture comprising one or more substituted or unsubstituted pentenals with hydrogen and carbon monoxide in the presence of a catalytic amount of a metal-ligand complex catalyst to produce said reaction mixture comprising one or more substituted or unsubstituted 1,6-hexanedials. In an embodiment, the step (a) hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. The hydroformylation reaction conditions in steps (a) and (b) may be the same or different and the hydroformylation catalysts in steps (a) and (b) may be the same or different.

The 1,6-hexanedials prepared according to the invention may undergo further derivatization. For example, further derivatization reactions include an oxidation, alkoxylation, reduction, hydrogenation, dehydrogenation, condensation, amination, esterification, etheration, silylation, alkylation, and acylation reaction. Advantageously, the 1,6-hexanedials may undergo cyclization to produce epsilon caprolactones. The epsilon caprolactones may be aminated to form epsilon caprolactams which may then be polymerized into nylon 6.

DETAILED DESCRIPTION

The hydroformylation process involves the production of aldehydes, e.g., 1,6-hexanedials or pentenals, by reacting an olefinic compound, e.g., pentenals or alkadienes, with carbon monoxide and hydrogen in the presence of a solubilized metal-ligand complex catalyst and free ligand in a liquid medium that also contains a solvent for the catalyst and ligand. The process may be carried out in a continuous single pass mode in a continuous gas recycle manner or more preferably in a continuous liquid catalyst recycle manner as described below. The hydroformylation processing techniques employable herein may correspond to any known processing techniques such as preferably employed in conventional liquid catalyst recycle hydroformylation reactions. As used herein, the term "hydroformylation" is contemplated to include, but not limited to, all permissible hydroformylation processes which involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes.

The hydroformylation reaction mixture starting materials employable herein includes any solution derived from any corresponding hydroformylation process that contains at least some amount of four different main ingredients or components, i.e., the aldehyde product, a metal-ligand complex catalyst, free ligand and an organic solubilizing agent for said catalyst and said free ligand, said ingredients corresponding to those employed and/or produced by the hydroformylation process from whence the hydroformylation reaction mixture starting material may be derived. By "free ligand" is meant ligand that is not complexed with (tied to or bound to) the metal, e.g., rhodium atom, of the complex catalyst. It is to be understood that the hydroformylation reaction mixture compositions employable herein can and normally will contain minor amounts of additional ingredients such as those which have either been deliberately employed in the hydroformylation process or formed in situ during said process. Examples of such ingredients that can also be present include unreacted olefin starting material, carbon monoxide and hydrogen gases, and in situ formed type products, such as saturated hydrocarbons and/or unreacted isomerized olefins corresponding to the olefin starting materials, and high boiling liquid aldehyde condensation byproducts, as well as other inert co-solvent type materials or hydrocarbon additives, if employed.

The catalysts useful in the hydroformylation process include metal-ligand complex catalysts. The permissible metals which make up the metal-ligand complexes include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. The permissible ligands include, for example, organophosphorus, organoarsenic and organoantimony ligands, or mixtures thereof, preferably organophosphorus ligands. The permissible organophosphorus ligands which make up the metal-ligand complexes include organophosphines, e.g., mono-, di-, tri- and poly-(organophosphines), and organophosphites, e.g., mono-, di-, tri- and poly-(organophosphites). Other permissible organophosphorus ligands include, for example, organophosphonites, organophosphinites, amino phosphines and the like. Still other permissible ligands include, for example, heteroatom-containing ligands such as described in U.S. patent application Ser. No. 08/818,781, filed Mar. 10, 1997, the disclosure of which is incorporated herein by reference. Mixtures of such ligands may be employed if desired in the metal-ligand complex catalyst and/or free ligand and such mixtures may be the same or different. This invention is not intended to be limited in any manner by the permissible organophosphorus ligands or mixtures thereof. It is to be noted that the successful practice of this invention does not depend and is not predicated on the exact structure of the metal-ligand complex species, which may be present in their mononuclear, dinuclear and/or higher nuclearity forms. Indeed, the exact structure is not known. Although it is not intended herein to be bound to any theory or mechanistic discourse, it appears that the catalytic species may in its simplest form consist essentially of the metal in complex combination with the ligand and carbon monoxide when used.

The term "complex" as used herein and in the claims means a coordination compound formed by the union of one or more electronically rich molecules or atoms capable of independent existence with one or more electronically poor molecules or atoms, each of which is also capable of independent existence. For example, the ligands employable herein, e.g., organophosphorus ligands, may possess one or more phosphorus donor atoms, each having one available or unshared pair of electrons which are each capable of forming a coordinate covalent bond independently or possibly in concert (e.g., via chelation) with the metal. Carbon monoxide (which is also properly classified as a ligand) can also be present and complexed with the metal. The ultimate composition of the complex catalyst may also contain an additional ligand, e.g., hydrogen or an anion satisfying the coordination sites or nuclear charge of the metal. Illustrative additional ligands include, e.g., halogen (Cl, Br, I), alkyl, aryl, substituted aryl, acyl, $CF_3$, $C_2F_5$, CN, $(R)_2PO$ and $RP(O)(OH)O$ (wherein each R is the same or different and is a substituted or unsubstituted hydrocarbon radical, e.g., the alkyl or aryl), acetate, acetylacetonate, $SO_4$, $BF_4$, $PF_6$, $NO_2$, $NO_3$, $CH_3O$, $CH_2=CHCH_2$, $CH_3CH=CHCH_2$, $C_6H_5CN$, $CH_3CN$, NO, $NH_3$, pyridine, $(C_2H_5)_3N$, mono-olefins, diolefins and triolefins, tetrahydrofuran, and the like. It is of course to be understood that the complex species are preferably free of any additional organic ligand or anion that might poison the catalyst and have an undue adverse effect on catalyst performance. It is preferred in the metal-ligand complex catalyzed hydroformylation reactions that the active catalysts be free of halogen and sulfur directly bonded to the metal, although such may not be absolutely necessary. Preferred metal-ligand complex catalysts include rhodium-organophosphine ligand complex catalysts and rhodium-organophosphite ligand complex catalysts.

The number of available coordination sites on such metals is well known in the art. Thus the catalytic species may comprise a complex catalyst mixture, in their monomeric, dimeric or higher nuclearity forms, which are preferably characterized by at least one phosphorus-containing molecule complexed per metal, e.g., rhodium. As noted above, it is considered that the catalytic species of the preferred catalyst employed in the hydroformylation reaction may be complexed with carbon monoxide and hydrogen in addition to the organophosphorus ligands in view of the carbon monoxide and hydrogen gas employed by the hydroformylation reaction.

Among the organophosphines that may serve as the ligand of the metal-organophosphine complex catalyst and/or free organophosphine ligand of the hydroformylation reaction mixture starting materials are triorganophosphines, trialkylphosphines, alkyldiarylphosphines, dialkylarylphosphines, dicycloalkylarylphosphines, cycloalkyldiarylphosphines, triaralkylphosphines, tricycloalkylphosphines, and triarylphosphines, alkyl and/or aryl diphosphines and bisphosphine mono oxides, as well as ionic triorganophosphines containing at least one ionic moiety selected from the salts of sulfonic acid, of carboxylic acid, of phosphonic acid and of quaternary ammonium compounds, and the like. Of course any of the hydrocarbon radicals of such tertiary non-ionic and ionic organophosphines may be substituted if desired, with any suitable substitutent that does not unduly adversely affect the desired result of the hydroformylation reaction. The organophosphine ligands employable in the hydroformylation reaction and/or methods for their preparation are known in the art.

Illustrative triorganophosphine ligands may be represented by the formula:

(I)

wherein each $R^1$ is the same or different and is a substituted or unsubstituted monovalent hydrocarbon radical, e.g., an alkyl or aryl radical. Suitable hydrocarbon radicals may contain from 1 to 24 carbon atoms or greater. Illustrative substituent groups that may be present on the aryl radicals include, e.g., alkyl radicals, alkoxy radicals, silyl radicals such as —$Si(R^2)_3$; amino radicals such as —$N(R^2)_2$; acyl radicals such as —$C(O)R^2$; carboxy radicals such as —$C(O)OR^2$; acyloxy radicals such as —$OC(O)R^2$; amido radicals such as —$C(O)N(R^2)_2$ and —$N(R^2)C(O)R^2$; ionic radicals such as —$SO_3M$ wherein M represents inorganic or organic cationic atoms or radicals; sulfonyl radicals such as —$SO_2R^2$; ether radicals such as —$OR^2$; sulfinyl radicals such as —$SOR^2$; sulfenyl radicals such as —$SR^2$ as well as halogen, nitro, cyano, trifluoromethyl and hydroxy radicals, and the like, wherein each $R^2$ individually represents the same or different substituted or unsubstituted monovalent hydrocarbon radical, with the proviso that in amino substituents such as —$N(R^2)_2$, each $R^2$ taken together can also represent a divalent bridging group that forms a heterocyclic radical with the nitrogen atom and in amido substituents such as $C(O)N(R^2)_2$ and —$N(R^2)C(O)R^2$ each —$R^2$ bonded to N can also be hydrogen. Illustrative alkyl radicals include, e.g., methyl, ethyl, propyl, butyl and the like. Illustrative aryl radicals include, e.g., phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl; carboxyphenyl, trifluoromethylphenyl, methoxyethylphenyl, acetamidophenyl, dimethylcarbamylphenyl, tolyl, xylyl, and the like.

Illustrative specific organophosphines include, e.g., triphenylphosphine, tris-p-tolyl phosphine, tris-p-methoxyphenylphosphine, tris-p-fluorophenylphosphine, tris-p-chlorophenylphosphine, tris-dimethylaminophenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine, DIOP, i.e., (4R,5R)-(−)—O-isopropylidene-2,3-dihydroxy-1,4-bis(diphenylphosphino)butane and/or (4S,5S)-(+)—O-isopropylidene-2,3-dihydroxy-1,4-bis(diphenylphosphino)butane and/or (4S,5R)-(−)—O-isopropylidene-2,3-dihydroxy-1,4-bis(diphenylphosphino)butane, substituted or unsubstituted bicyclic bisphosphines such as 1,2-bis(1,4-cyclooctylenephosphino)ethane, 1,3-bis(1,4-cyclooctylenephosphino)propane, 1,3-bis(1,5-cyclooctylenephosphino)propane and 1,2-bis(2,6-dimethyl-1,4-cyclooctylenephosphino)ethane, substituted or unsubstituted bis(2,2'-diphenylphosphinomethyl)biphenyl such as bis(2,2'-diphenylphosphinomethyl)biphenyl and bis{2,2'-di(4-fluorophenyl)phosphinomethyl}biphenyl, xantphos, thixantphos, bis(diphenylphosphino)ferrocene, bis(diisopropylphosphino)ferrocene, bis(diphenylphosphino)ruthenocene, as well as the alkali and alkaline earth metal salts of sulfonated triphenylphosphines, e.g., of (tri-m-sulfophenyl)phosphine and of (m-sulfophenyl)diphenyl-phosphine and the like.

More particularly, illustrative metal-organophosphine complex catalysts and illustrative free organophosphine ligands include, e.g., those disclosed in U.S. Pat. Nos. 3,527,809; 4,148,830; 4,247,486; 4,283,562; 4,400,548; 4,482,749, 4,861,918; 4,694,109; 4,742,178; 4,851,581; 4,824,977; 5,332,846; 4,774,362; and WO Patent Application No. 95/30680, published Nov. 16, 1995; the disclosures of which are incorporated herein by reference.

The organophosphites that may serve as the ligand of the metal-organophosphite ligand complex catalyst and/or free ligand of the processes and reaction product mixtures of this invention may be of the achiral (optically inactive) or chiral (optically active) type and are well known in the art.

Among the organophosphites that may serve as the ligand of the metal-organophosphite complex catalyst and/or free organophosphite ligand of the hydroformylation reaction mixture starting materials are monoorganophosphites, diorganophosphites, triorganophosphites and organopolyphosphites. The organophosphite ligands employable in this invention and/or methods for their preparation are known in the art.

Representative monoorganophosphites may include those having the formula:

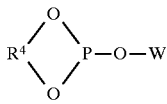
(II)

wherein $R^3$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane, and the like. Such monoorganophosphites may be found described in greater detail, e.g., in U.S. Pat. No. 4,567,306, the disclosure of which is incorporated herein by reference.

Representative diorganophosphites may include those having the formula:

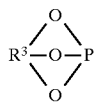
(III)

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above formula (III) include alkyl and aryl radicals, while representative substituted and unsubstituted divalent hydrocarbon radicals represented by $R^4$ include divalent acyclic radicals and divalent aromatic radicals. Illustrative divalent acyclic radicals include, e.g., alkylene, alkylene-oxy-alkylene, alkylene-NX-alkylene wherein X is hydrogen or a substituted or unsubstituted monovalent hydrocarbon radical, alkylene-S-alkylene, and cycloalkylene radicals, and the like. The more preferred divalent acyclic radicals are the divalent alkylene radicals such as disclosed more fully, e.g., in U.S. Pat. Nos. 3,415,906 and 4,567,302 and the like, the disclosures of which are incorporated herein by reference. Illustrative divalent aromatic radicals include, e.g., arylene, bisarylene, arylene-alkylene, arylene-alkylene-arylene, arylene-oxy-arylene, arylene-NX-arylene wherein X is as defined above, arylene-S-arylene, and arylene-S-alkylene, and the like. More preferably $R^4$ is a divalent aromatic radical such as disclosed more fully, e.g., in U.S. Pat. Nos. 4,599,206 and 4,717,775, and the like, the disclosures of which are incorporated herein by reference.

Representative of a more preferred class of diorganophosphites are those of the formula:

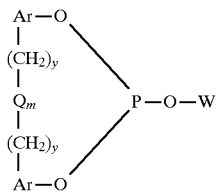
(IV)

wherein W is as defined above, each Ar is the same or different and represents a substituted or unsubstituted aryl radical, each y is the same or different and is a value of 0 or 1, Q represents a divalent bridging group selected from —C($R^5$)$_2$—, —O—, —S—, —N$R^6$—, Si($R^7$)$_2$— and —CO—, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1. Such diorganophosphites are described in greater detail, e.g., in U.S. Pat. Nos. 4,599,206 and 4,717,775, the disclosures of which are incorporated herein by reference.

Representative triorganophosphites may include those having the formula:

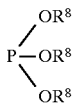
(V)

wherein each $R^8$ is the same or different and is a substituted or unsubstituted monovalent hydrocarbon radical, e.g., an alkyl or aryl radical. Suitable hydrocarbon radicals may contain from 1 to 24 carbon atoms or greater and may include those described above for $R^1$ in formula (I).

Representative organopolyphosphites contain two or more tertiary (trivalent) phosphorus atoms and may include those having the formula:

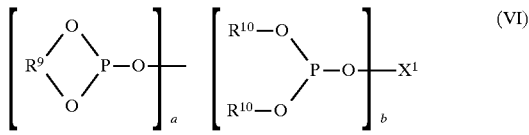

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. Of course it is to be understood that when a has a value of 2 or more, each $R^9$ radical may be the same or different, and when b has a value of 1 or more, each $R^{10}$ radical may also be the same or different.

Representative n-valent (preferably divalent) hydrocarbon bridging radicals represented by $X^1$, as well as representative divalent hydrocarbon radicals represented by $R^9$ above, include both acyclic radicals and aromatic radicals, such as alkylene, alkylene-$Q_m$-alkylene, cycloalkylene, arylene, bisarylene, arylene-alkylene, and arylene-$(CH_2)_y$-$Q_m$-$(CH_2)_y$-arylene radicals, and the like, wherein Q, m and y are as defined above for formula (IV). The more preferred acyclic radicals represented by $X^1$ and $R^9$ above are divalent alkylene radicals, while the more preferred aromatic radicals represented by $X^1$ and $R^9$ above are divalent arylene and bisarylene radicals, such as disclosed more fully, e.g., in U.S. Pat. Nos. 3,415,906; 4,567,306; 4,599,206; 4,769,498; 4,717,775; 4,885,401; 5,202,297; 5,264,616 and 5,364,950, and the like, the disclosures of which are incorporated herein by reference. Representative monovalent hydrocarbon radicals represented by each $R^{10}$ radical above include alkyl and aromatic radicals.

Illustrative preferred organopolyphosphites may include bisphosphites such as those of formulas (VII) to (IX) below:

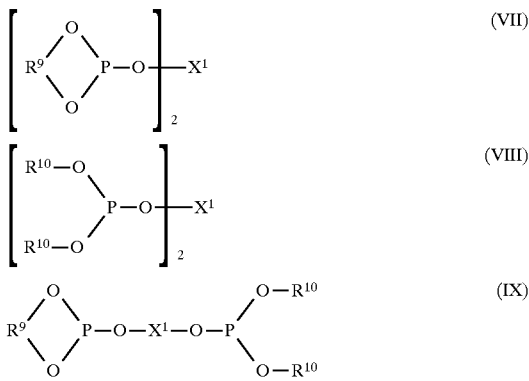

wherein each $R^9$, $R^{10}$ and $X^1$ of formulas (VII) to (IX) are the same as defined above for formula (VI). Preferably, each $R^9$ and $X^1$ represents a divalent hydrocarbon radical selected from alkylene, arylene, arylene-alkylene-arylene, and bisarylene, while each $R^{10}$ represents a monovalent hydrocarbon radical selected from alkyl and aryl radicals. Phosphite ligands of such formulas (VI) to (IX) may be found disclosed, e.g., in said U.S. Pat. Nos. 4,668,651; 4,748,261; 4,769,498; 4,885,401; 5,202,297; 5,235,113; 5,254,741; 5,264,616; 5,312,996; 5,364,950; and 5,391,801; the disclosures of all of which are incorporated herein by reference.

Representative of more preferred classes of organobisphosphites are those of the following formulas (X) to (XII):

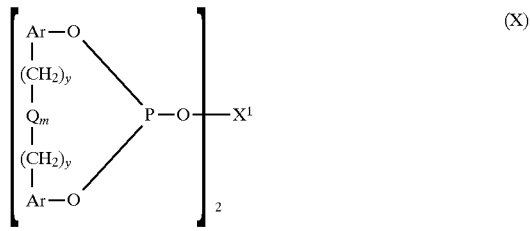

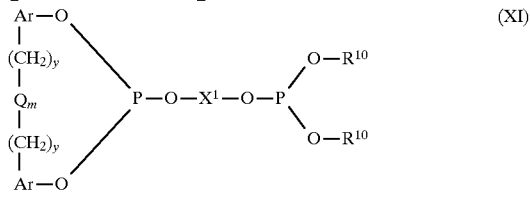

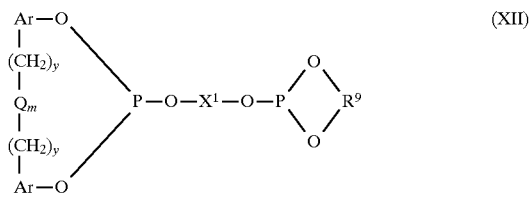

wherein Ar, Q $R^9$, $R^{10}$, $X^1$, m and y are as defined above. Most preferably $X^1$ represents a divalent aryl-$(CH_2)_y$-$(Q)_m$-$(CH_2)_y$-aryl radical wherein each y individually has a value of 0 or 1; m has a value of 0 or 1 and Q is —O—, —S— or —$C(R^5)_2$— wherein each $R^5$ is the same or different and represents a hydrogen or methyl radical. More preferably each alkyl radical of the above defined $R^{10}$ groups may contain from 1 to 24 carbon atoms and each aryl radical of the above-defined Ar, $X^1$, $R^9$ and $R^{10}$ groups of the above formulas (VI) to (XII) may contain from 6 to 18 carbon atoms and said radicals may be the same or different, while the preferred alkylene radicals of $X^1$ may contain from 2 to 18 carbon atoms and the preferred alkylene radicals of $R^9$ may contain from 5 to 18 carbon atoms. In addition, preferably the divalent Ar radicals and divalent aryl radicals of $X^1$ of the above formulas are phenylene radicals in which the bridging group represented by —$(CH_2)_y$—$(Q)_m$—$(CH_2)_y$— is bonded to said phenylene radicals in positions that are ortho to the oxygen atoms of the formulas that connect the phenylene radicals to their phosphorus atom of the formulas. It is also preferred that any substituent radical when present on such phenylene radicals be bonded in the para and/or ortho position of the phenylene radicals in relation to the oxygen atom that bonds the given substituted phenylene radical to its phosphorus atom.

Moreover, if desired any given organophosphite in the above formulas (VI) to (XII) may be an ionic phosphite, i.e., may contain one or more ionic moieties selected from the group consisting of:

$SO_3M$ wherein M represents inorganic or organic cation, $PO_3M$ wherein M represents inorganic or organic cation, N(R¹¹)₃X² wherein each R¹¹ is the same or different and represents a hydrocarbon radical containing from 1 to 30 carbon atoms, e.g., alkyl, aryl, alkaryl, aralkyl, and cycloalkyl radicals, and X² represents inorganic or organic anion, CO₂M wherein M represents inorganic or organic cation, as described, e.g., in U.S. Pat. Nos. 5,059,710; 5,113,022, 5,114,473 and 5,449,653, the disclosures of which are incorporated herein by reference. Thus, if desired, such phosphite ligands may contain from 1 to 3 such ionic moieties, while it is preferred that only one such ionic moiety be substituted on any given aryl moiety in the phosphite ligand when the ligand contains more than one such ionic moiety. As suitable counter-ions, M and X², for the anionic moieties of the ionic phosphites there can be mentioned hydrogen (i.e., a proton), the cations of the alkali and alkaline earth metals, e.g., lithium, sodium, potassium, cesium, rubidium, calcium, barium, magnesium and strontium, the ammonium cation, quaternary ammonium cations, phosphonium cations, arsonium cations and iminium cations. Suitable anionic groups include, for example, sulfate, carbonate, phosphate, chloride, acetate, oxalate and the like.

Of course any of the R⁹, R¹⁰, X² and Ar radicals of such non-ionic and ionic organophosphites of formulas (VI) to (XII) above may be substituted if desired, with any suitable substituent containing from 1 to 30 carbon atoms that does not unduly adversely affect the desired result of the hydroformylation reaction. Substituents that may be on said radicals in addition of course to corresponding hydrocarbon radicals such as alkyl, aryl, aralkyl, alkaryl and cyclohexyl substituents, may include for example silyl radicals such as —Si(R¹²)₃; amino radicals such as —N(R¹²)₂; phosphine radicals such as -aryl-P(R¹²)₂; acyl radicals such as —C(O) R¹²; acyloxy radicals such as —OC(O)R¹²; amido radicals such as —CON(R¹²)₂ and —N(R¹²)COR¹²; sulfonyl radicals such as —SO₂R¹²; alkoxy radicals such as —OR¹²; sulfinyl radicals such as —SOR¹²; sulfenyl radicals such as —SR¹²; phosphonyl radicals such as —P(O)(R¹²)₂; as well as, halogen, nitro, cyano, trifluoromethyl, hydroxy radicals, and the like, wherein each R¹² radical is the same or different and represents a monovalent hydrocarbon radical having from 1 to 18 carbon atoms (e.g., alkyl, aryl, aralkyl, alkaryl and cyclohexyl radicals), with the proviso that in amino substituents such as —N(R¹²)₂ each R¹² taken together can also represent a divalent bridging group that forms a heterocyclic radical with the nitrogen atom, and in amido substituents such as —C(O)N(R¹²)₂ and —N(R¹²)COR¹² each R¹² bonded to N can also be hydrogen. Of course it is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —OCH₂CH₂OCH₃, —(OCH₂CH₂)₂OCH₃, —(OCH₂CH₂)₃OCH₃, and the like; aryloxy radicals such as phenoxy and the like; as well as silyl radicals such as —Si(CH₃)₃, —Si(OCH₃)₃, —Si(C₃H₇)₃, and the like; amino radicals such as —NH₂, —N(CH₃)₂, —NHCH₃, —NH(C₂H₅), and the like; arylphosphine radicals such as —P(C₆H₅)₂, and the like; acyl radicals such as —C(O)CH₃, —C(O)C₂H₅, —C(O) C₆H₅, and the like; carbonyloxy radicals such as —C(O) OCH₃ and the like; oxycarbonyl radicals such as —O(CO) C₆H₅, and the like; amido radicals such as —CONH₂, —CON(CH₃)₂, —NHC(O)CH₃, and the like; sulfonyl radicals such as —S(O)₂C₂H₅ and the like; sulfinyl radicals such as —S(O)CH₃ and the like; sulfenyl radicals such as —SCH₃, —SC₂H₅, —SC₆H₅, and the like; phosphonyl radicals such as —P(O)(C₆H₅)₂, —P(O)(CH₃)₂, —P(O) (C₂H₅)₂, —P(O)(C₃H₇)₂, —P(O)(C₄H₉)₂, —P(O)(C₆H₁₃)₂, —P(O)CH₃(C₆H₅), —P(O)(H)(C₆H₅), and the like.

Specific illustrative examples of such organophosphite ligands include the following:

2-t-butyl-4-methoxyphenyl(3,3'-di-t-butyl-5,5'-dimethoxy-1,1'-biphenyl-2,2'-diyl)phosphite having the formula:

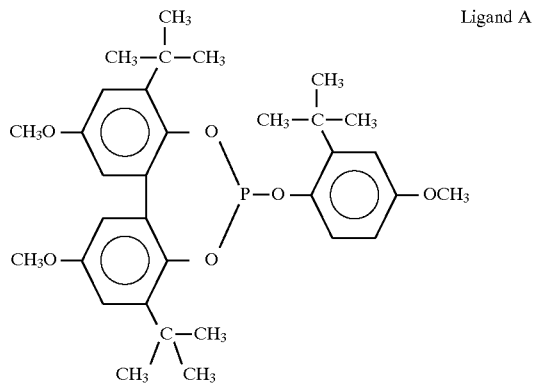

Ligand A methyl(3,3'-di-t-butyl-5,5'-dimethoxy-1,1'-biphenyl-2,2'-diyl)phosphite having the formula:

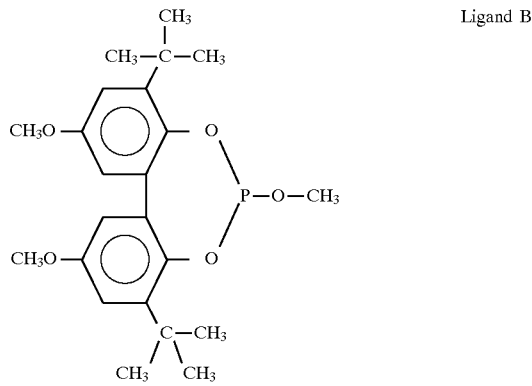

Ligand B 6,6'-[[4,4'-bis(1,1-dimethylethyl)-[1,1'-binaphthyl]-2,2'-diyl]bis(oxy)]bis-dibenzo[d,f][1,3,2]-dioxaphosphepin having the formula:

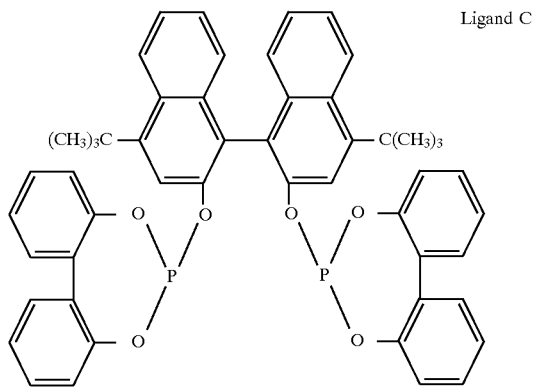

6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin having the formula:

Ligand C

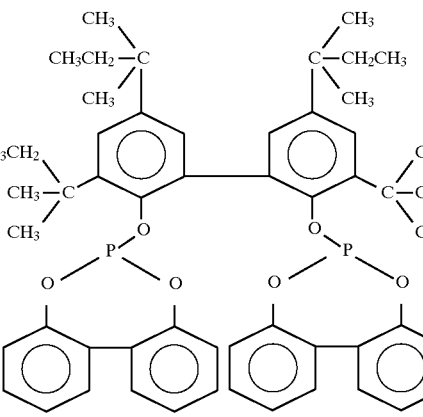

6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin having the formula:

Ligand E

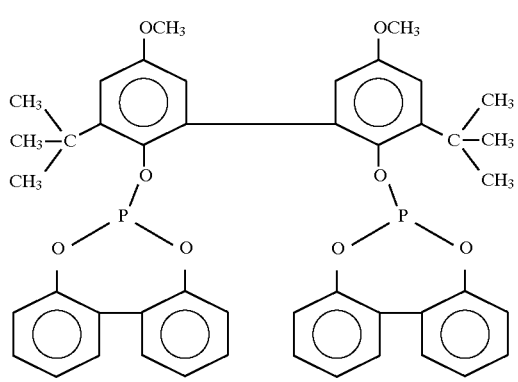

6,6'-[[3,3',5,5'-tetrakis(1,1-dimethylpropyl)-[1,1'-biphenyl]-2,2'-diyl]bis(oxy)]bis-dibenzo[d,f][1,3,2]dioxaphosphepin having the formula:

Ligand D

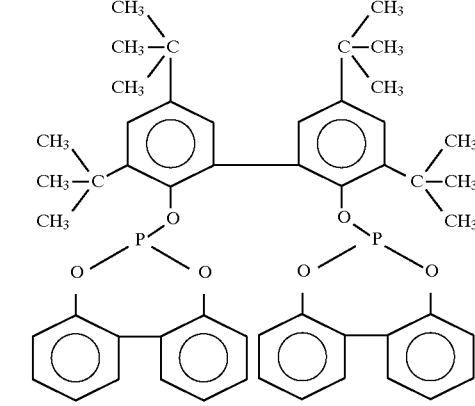

(2R,4R)-di[2,2'-(3,3',5,5'-tetrakis-tert-amyl-1,1'-biphenyl)]-2,4-pentyldiphosphite having the formula:

Ligand F

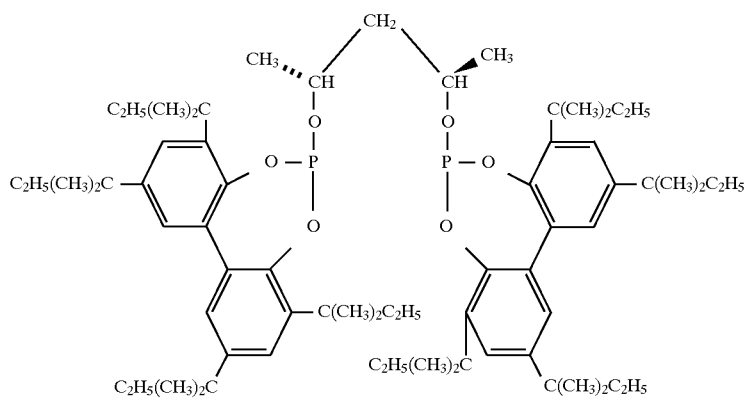

(2R,4R)-di [2,2'-(3,3',5,5'-tetrakis-tert-butyl-1,1'-biphenyl)]-2,4-pentyldiphosphite having the formula:

Ligand G

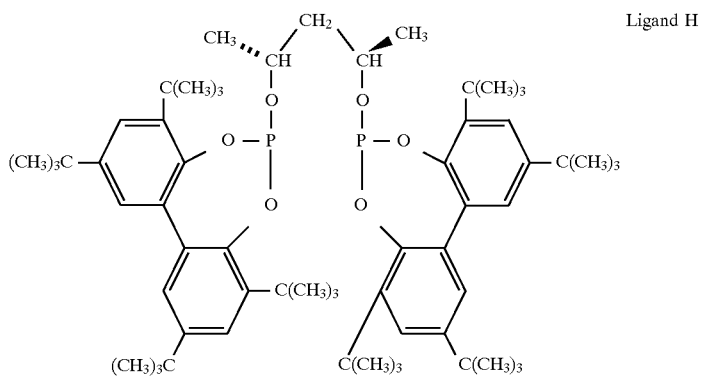
Ligand H
(2R,4R)-di[2,2'-(3,3'-di-amyl-5,5'-dimethoxy-1,1'-biphenyl)]-2,4-pentyldiphosphite having the formula:
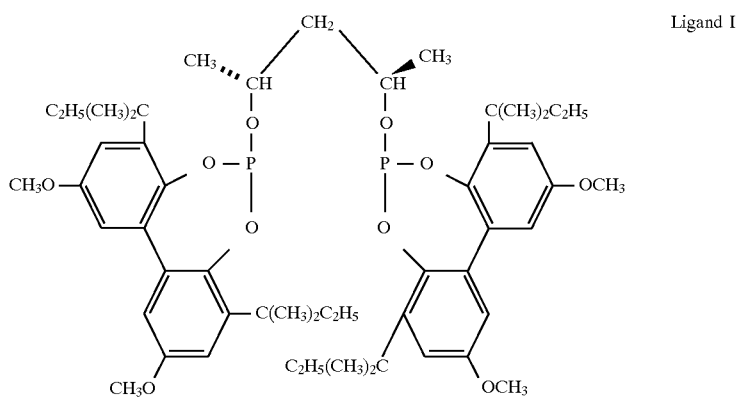
Ligand I
(2R,4R)-di[2,2'-(3,3'-di-tert-butyl-5,5'-dimethyl-1,1'-biphenyl)]-2,4-pentyldiphosphite having the formula:
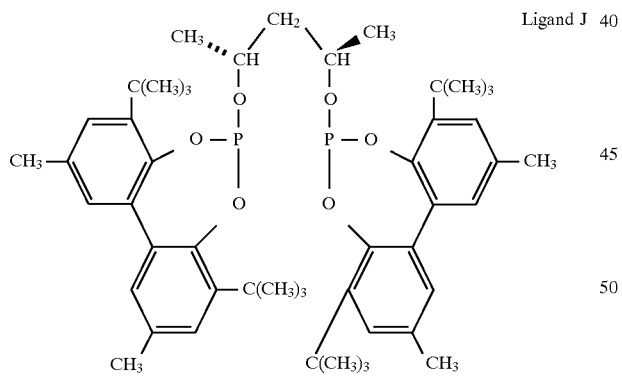
Ligand J
(2R,4R)-di[2,2'-(3,3'-di-tert-butyl-5,5'-diethoxy-1,1'-biphenyl)]-2,4-pentyldiphosphite having the formula:

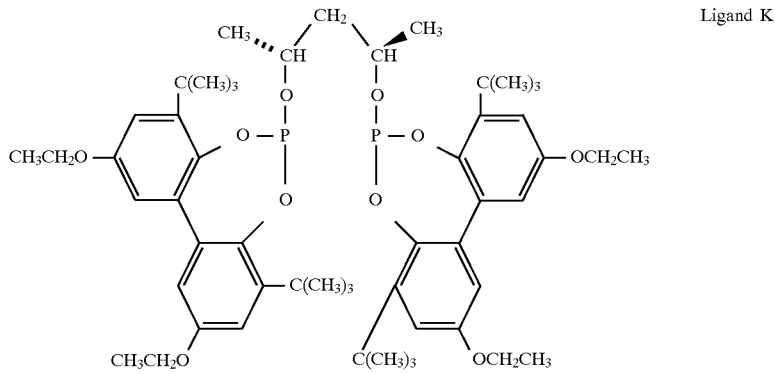

Ligand K (2R,4R)-di[2,2'-(3,3'-di-tert-butyl-5,5'-diethyl-1,1'-biphenyl)]-2,4-pentyldiphosphite having the formula:

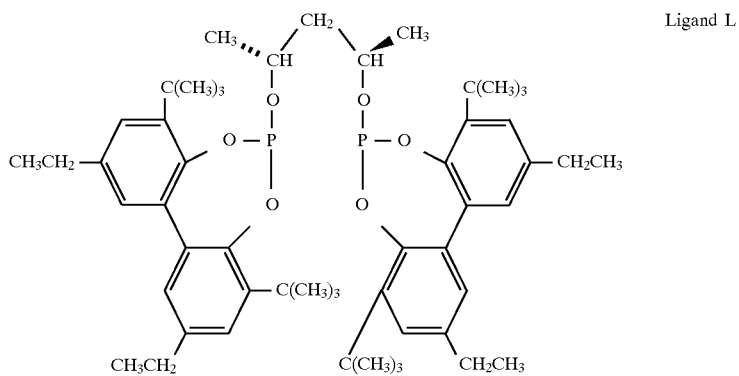

Ligand L (2R,4R)-di[2,2'-(3,3'-di-tert-butyl-5,5'-dimethoxy-1,1'-biphenyl)]-2,4-pentyldiphosphite having the formula:

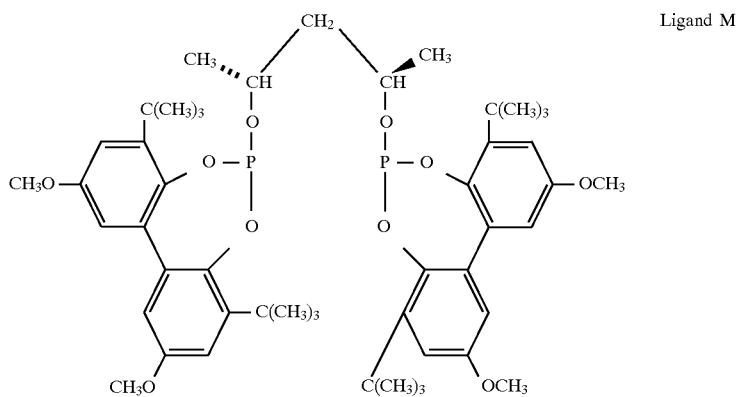

Ligand M

6-[[2'-[(4,6-bis(1,1-dimethylethyl)-1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

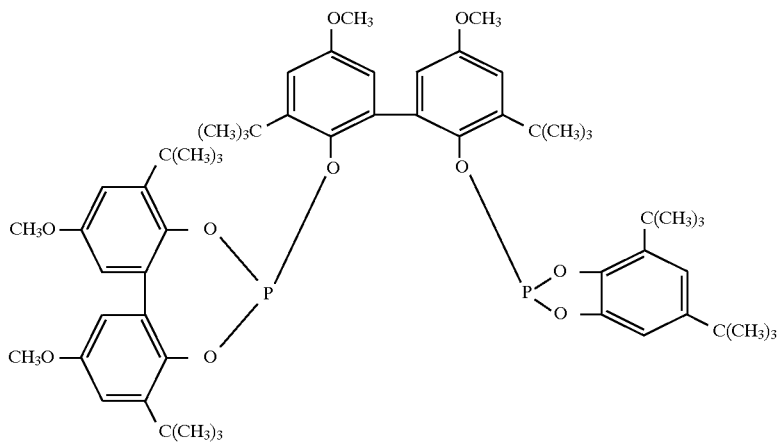

Ligand N

6-[[2'-[1,3,2-benzodioxaphosphol-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

2'-[[4,8-bis(1,1-dimethylethyl)-2,10-dimethoxydibenzo[d,f][1,3,2]-dioxaphosphepin-6-yl]oxy]-3,3'-bis(1,1-dimethylethyl)-5,5'-dimethoxy[1,1'-biphenyl]-2-yl bis(4-hexylphenyl)ester of phosphorous acid having the formula:

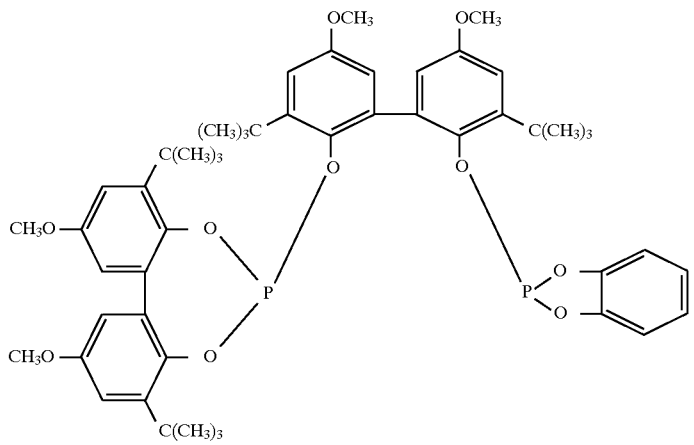

Ligand O

6-[[2'-[(5,5-dimethyl-1,3,2-dioxaphosphorinan-2-yl)oxy]-3,3'-bis(1,1-dimethylethyl)-5,5'-dimethoxy[1,1'-biphenyl]-2-yl]oxy]-4,8-bis(1,1-dimethylethyl)-2,10-dimethoxydibenzo[d,f][1,3,2]dioxaphosphepin having the formula:

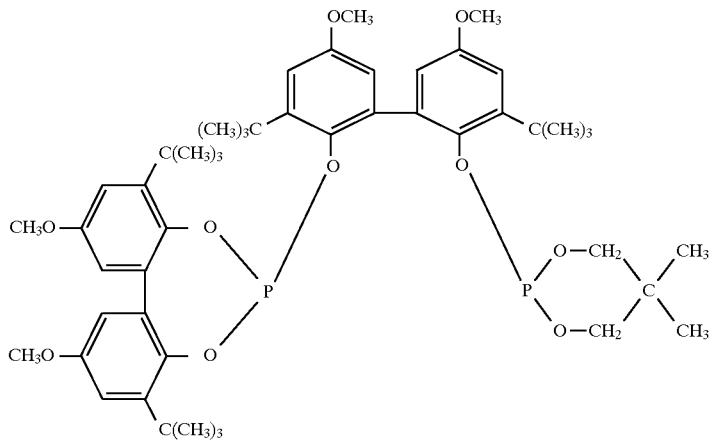

Ligand P

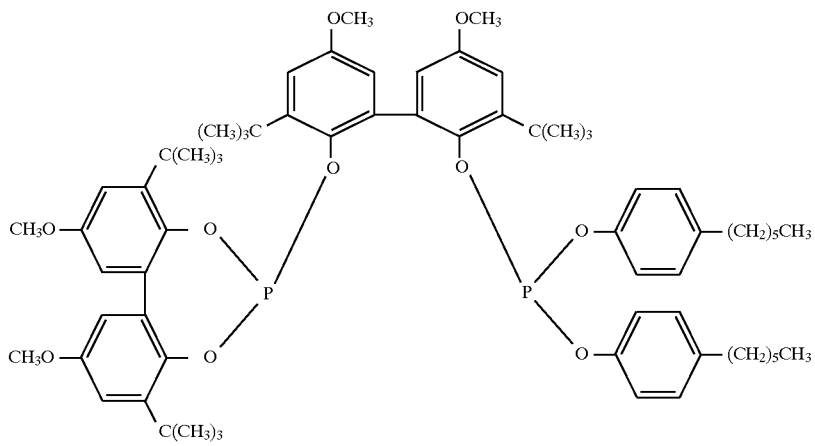

Ligand Q

2-[[2-[[4,8,-bis(1,1-dimethylethyl), 2,10-dimethoxydibenzo-[d,f][1,3,2]dioxophosphepin-6-yl]oxy-3-(1,1-dimethylethyl)-5-methoxyphenyl]methyl]-4-methoxy, 6-(1,1-dimethylethyl)phenyl diphenyl ester of phosphorous acid having the formula:

2,5-bis(1,1-dimethylethyl)-1,4-phenylene tetrakis[2,4-bis(1,1-dimethylethyl)phenyl]ester of phosphorous acid having the formula:

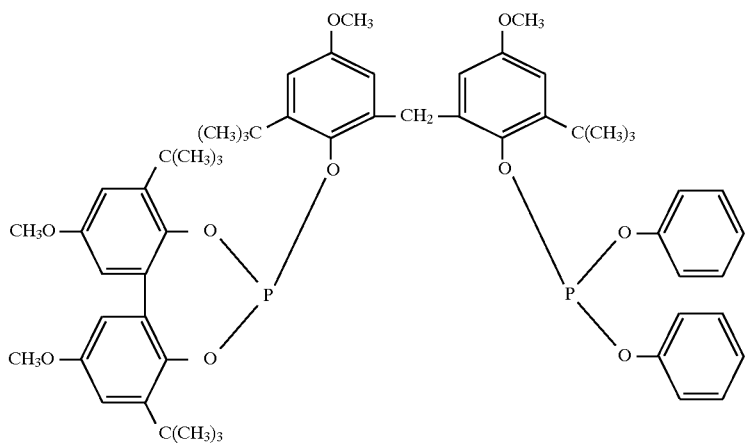

Ligand R 3-methoxy-1,3-cyclohexamethylene tetrakis [3,6-bis(1,1-dimethylethyl)-2-naphthalenyl]ester of phosphorous acid having the formula:

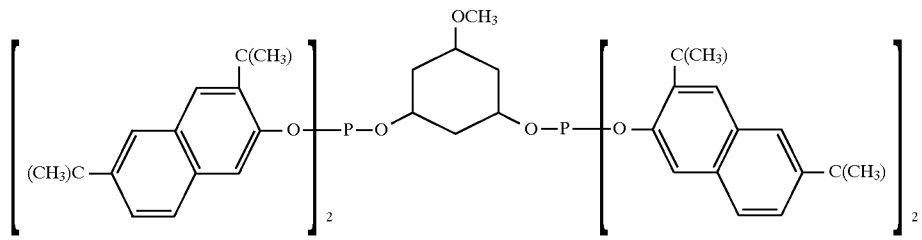

Ligand S

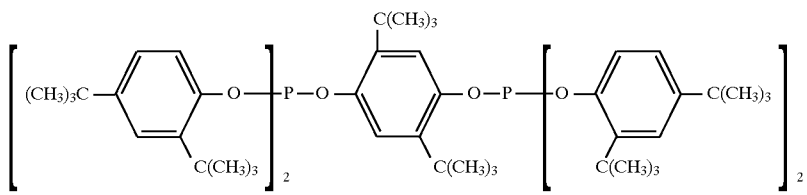

Ligand T methylenedi-2,1-phenylene tetrakis[2,4-bis(1,1-dimethylethyl)phenyl]ester of phosphorous acid having the formula:

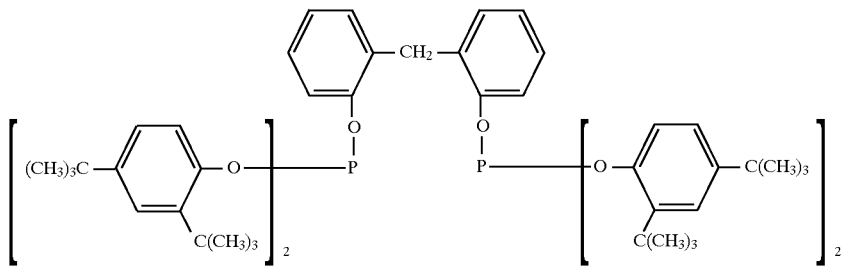

Ligand U

[1,1'-biphenyl]-2,2'-diyl tetrakis [2-(1,1-dimethylethyl)-4-methoxyphenyl]ester of phosphorous acid having the formula:

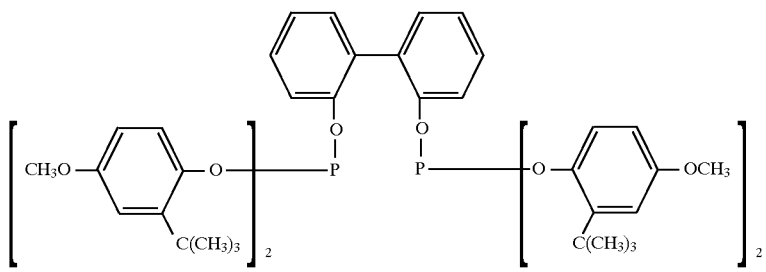

Ligand V

Still other illustrative organophosphorus ligands useful in this invention include those disclosed in U.S. patent application Ser. No. 08/843,389, filed on an even date herewith, the disclosure of which is incorporated herein by reference.

The metal-ligand complex catalysts employable in this invention may be formed by methods known in the art. The metal-ligand complex catalysts may be in homogeneous or heterogeneous form. For instance, preformed metal hydridocarbonyl-organophosphorus ligand catalysts may be prepared and introduced into the reaction mixture of a hydroformylation process. More preferably, the metal-ligand complex catalysts can be derived from a metal catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorus ligand for the in situ formation of the active catalyst. In a preferred embodiment of this invention, rhodium dicarbonyl acetylacetonate is employed as a rhodium precursor and reacted in the presence of a solvent with the organophosphorus ligand to form a catalytic rhodium-organophosphorus ligand complex precursor which is introduced into the reactor along with excess free organophosphorus ligand for the in situ formation of the active catalyst. In any event, it is sufficient for the purpose of this invention that carbon monoxide, hydrogen and organophosphorus compound are all ligands that are capable of being complexed with the metal and that an active metal-organophosphorus ligand catalyst is present in the reaction mixture under the conditions used in the hydroformylation reaction.

More particularly, a catalyst precursor composition can be formed consisting essentially of a solubilized metal-ligand complex precursor catalyst, an organic solvent and free ligand. Such precursor compositions may be prepared by forming a solution of a metal starting material, such as a metal oxide, hydride, carbonyl or salt, e.g., a nitrate, which may or may not be in complex combination with a ligand as defined herein. Any suitable metal starting material may be employed, e.g., rhodium dicarbonyl acetylacetonate, $Rh_2O_3$, $Rh_4(CO)_{12}$, $Rh_6(CO)_{16}$, $Rh(NO_3)_3$, and organophosphorus ligand rhodium carbonyl hydrides. Carbonyl and organophosphorus ligands, if not already complexed with the initial metal, may be complexed to the metal either prior to or in situ during the hydroformylation process.

By way of illustration, the preferred catalyst precursor composition of this invention consists essentially of a solubilized rhodium carbonyl organophosphorus ligand complex precursor catalyst, a solvent and free organophosphorus ligand prepared by forming a solution of rhodium dicarbonyl acetylacetonate, an organic solvent and an organophosphorus ligand as defined herein. The organophosphorus ligand readily replaces one of the carbonyl ligands of the rhodium acetylacetonate complex precursor at room temperature as witnessed by the evolution of carbon monoxide gas. This substitution reaction may be facilitated by heating the solution if desired. Any suitable organic solvent in which both the rhodium dicarbonyl acetylacetonate complex precursor and rhodium organophosphorus ligand complex precursor are soluble can be employed. The amounts of rhodium complex catalyst precursor, organic solvent and organophosphorus ligand, as well as their preferred embodiments present in such catalyst precursor compositions may obviously correspond to those amounts employable in the hydroformylation process of this invention. Experience has shown that the acetylacetonate ligand of the precursor catalyst is replaced after the hydroformylation process has begun with a different ligand, e.g., hydrogen, carbon monoxide or organophosphorus ligand, to form the active complex catalyst as explained above. In a continuous process, the acetylacetone which is freed from the precursor catalyst under hydroformylation conditions is removed from the reaction medium with the product aldehyde and thus is in no way detrimental to the hydroformylation process. The use of such preferred rhodium complex catalytic precursor compositions provides a simple economical and efficient method for handling the rhodium precursor metal and hydroformylation start-up.

Accordingly, the metal-ligand complex catalysts used in the process of this invention consists essentially of the metal complexed with carbon monoxide and a ligand, said ligand being bonded (complexed) to the metal in a chelated and/or non-chelated fashion. Moreover, the terminology "consists essentially of", as used herein, does not exclude, but rather includes, hydrogen complexed with the metal, in addition to carbon monoxide and the ligand. Further, such terminology does not exclude the possibility of other organic ligands and/or anions that might also be complexed with the metal. Materials in amounts which unduly adversely poison or unduly deactivate the catalyst are not desirable and so the catalyst most desirably is free of contaminants such as metal-bound halogen (e.g., chlorine, and the like) although such may not be absolutely necessary. The hydrogen and/or carbonyl ligands of an active metal-organophosphorus ligand complex catalyst may be present as a result of being ligands bound to a precursor catalyst and/or as a result of in situ formation, e.g., due to the hydrogen and carbon monoxide gases employed in hydroformylation process of this invention.

As noted the hydroformylation reactions involve the use of a metal-ligand complex catalyst as described herein. Of course mixtures of such catalysts can also be employed if desired. The amount of metal-ligand complex catalyst present in the reaction medium of a given hydroformylation reaction need only be that minimum amount necessary to provide the given metal concentration desired to be employed and which will furnish the basis for at least the catalytic amount of metal necessary to catalyze the particular hydroformylation reaction involved such as disclosed e.g., in the above-mentioned patents. In general, the catalyst concentration can range from several parts per million to several percent by weight. Organophosphorus ligands can be employed in the above-mentioned catalysts in a molar ratio of generally from about 0.5:1 or less to about 1000:1 or greater. The catalyst concentration will be dependent on the hydroformylation reaction conditions and solvent employed.

In general, the ligand concentration in hydroformylation reaction mixtures may range from between about 0.005 and 25 weight percent based on the total weight of the reaction mixture. Preferably the ligand concentration is between 0.01 and 15 weight percent, and more preferably between about 0.05 and 10 weight percent.

In general, the concentration of the metal in the hydroformylation reaction mixtures may be as high as about 2000 parts per million by weight or greater based on the weight of the reaction mixture. Preferably the metal concentration is between about 50 and 1000 parts per million by weight based on the weight of the reaction mixture, and more preferably is between about 70 and 800 parts per million by weight based on the weight of the reaction mixture.

In addition to the metal-ligand complex catalyst, free ligand (i.e., ligand that is not complexed with the metal) is also present in the hydroformylation reaction medium. The free ligand may correspond to any of the ligands discussed above. The free ligand is preferably the same as the ligand of the metal-ligand complex catalyst. However, the ligands need not be the same in any given process. The hydroformylation reaction may involve up to 100 moles, or higher, of free ligand per mole of metal in the hydroformylation reaction medium. Preferably the hydroformylation reaction is carried out in the presence of from about 0.25 to about 50 moles of coordinatable phosphorus, and more preferably from about 0.5 to about 4 moles of coordinatable phosphorus, per mole of metal present in the reaction medium. The amount of coordinatable phosphorus is the sum of the amount of coordinatable phosphorus that is bound (complexed) to the rhodium metal and the amount of free (non-complexed) coordinatable phosphorus present. Of course, if desired, make-up or additional coordinatable phosphorus can be supplied to the reaction medium of the hydroformylation reaction at any time and in any suitable manner, e.g., to maintain a predetermined level of free ligand in the reaction medium.

As indicated above, the hydroformylation catalyst may be in heterogeneous form during the reaction and/or during the product separation. Such catalysts are particularly advantageous in the hydroformylation of olefins to produce high boiling or thermally sensitive aldehydes, so that the catalyst may be separated from the products by filtration or decantation at low temperatures. For example, the catalyst may be attached to a support so that the catalyst retains its solid form during both the hydroformylation and separation stages, or is soluble in a liquid reaction medium at high temperatures and then is precipitated on cooling.

As an illustration, a rhodium catalyst may be impregnated onto a solid support, such as inorganic oxides, (i.e., alumina, silica, titania, or zirconia) carbon, or ion exchange resins. The catalyst may be supported on, or intercalated inside the pores of, a zeolite or glass. The catalyst may also be dissolved in a liquid film coating the pores of the zeolite or glass. Such zeolite-supported catalysts are particularly advantageous for producing one or more regioisomeric aldehydes in high selectivity, as determined by the pore size of the zeolite. The techniques for supporting catalysts on solids, such as incipient wetness, are known to those skilled in the art. The solid catalyst thus formed may still be complexed with one or more of the ligands defined above. Descriptions of such solid catalysts may be found in for example: J. Mol. Cat. 1991, 70, 363–368; Catal. Lett. 1991, 8, 209–214; J. Organomet. Chem, 1991, 403, 221–227; Nature, 1989, 339, 454–455; J. Catal. 1985, 96, 563–573; J. Mol. Cat. 1987, 39, 243–259.

The hydroformylation catalyst, for example a rhodium catalyst, may be attached to a thin film or membrane support, such as polyphenylenesulfone or cellulose acetate as described in for example J. Mol. Cat. 1990, 63, 213–221.

The hydroformylation (e.g., rhodium) catalyst may be attached to an insoluble polymeric support through an organophosphorus-containing ligand, such as a phosphine or phosphite, incorporated into the polymer. Such polymer-supported ligands are well known, and include such commercially available species as the divinylbenzene/polystyrene-supported triphenylphosphine. The supported ligand is not limited by the choice of polymer or phosphorus-containing species. Polymer-supported catalysts are described in, for example: J. Mol. Cat. 1993, 83, 17–35; Chemtech 1983, 46; J. Am. Chem. Soc. 1987, 109, 7122–7127.

In the heterogeneous catalysts described above, the catalyst may remain in its heterogeneous form during the entire hydroformylation and catalyst separation process. In another embodiment of the invention, the catalyst may be supported on a polymer which, by the nature of its molecular weight, is soluble in the reaction medium at elevated temperatures, but precipitates upon cooling, thus facilitating catalyst separation from the reaction mixture. Such "soluble" polymer-supported catalysts are described in for example: Polymer, 1992, 33, 161; J. Org. Chem. 1989, 54, 2726–2730.

When the rhodium catalyst is in a heterogeneous or supported form, the reaction may be carried out in the gas phase. More preferably, the reaction is carried out in the slurry phase due to the high boiling points of the products, and to avoid decomposition of the product aldehydes. The catalyst may then be separated from the product mixture by filtration or decantation.

The substituted and unsubstituted alkadiene starting materials useful in the hydroformylation reactions include, but are not limited to, conjugated aliphatic olefins represented by the formula:

(XIII)

wherein $R_1$ and $R_2$ are the same or different and are hydrogen, halogen or a substituted or unsubstituted hydrocarbon radical. The alkadienes can be linear or branched and can contain substituents (e.g., alkyl groups, halogen atoms, amino groups or silyl groups). Illustrative of suitable alkadiene starting materials are butadiene, isoprene, dimethyl butadiene and cyclopentadiene. Most preferably, the alkadiene starting material is butadiene itself ($CH_2$=CH—CH=$CH_2$). For purposes of this invention, the term "alkadiene" is contemplated to include all permissible substituted and unsubstituted alkadienes, including all permissible mixtures comprising one or more substituted or unsubstituted alkadienes. Illustrative of suitable substituted and unsubstituted alkadienes (including derivatives of alkadienes) include those permissible substituted and unsubstituted alkadienes described in Kirk-Othmer, Encyclopedia of Chemical Technology, Fourth Edition, 1996, the pertinent portions of which are incorporated herein by reference.

The hydroformylation reaction conditions may include any suitable hydroformylation conditions heretofore employed for producing aldehydes. For instance, the total gas pressure of hydrogen, carbon monoxide and olefin starting compound of the hydroformylation process may range from about 1 to about 10,000 psia. In general, the hydroformylation process is operated at a total gas pressure of hydrogen, carbon monoxide and olefin starting compound of less than about 1500 psia and more preferably less than about 1000 psia. The minimum total pressure is limited predominately by the amount of reactants needed to obtain a desired rate of reaction. The total pressure employed in the alkadiene hydroformylation reaction may range in general from about 20 to about 2000 psia, preferably from about 50 to 1500 psia and more preferably from about 75 to about 1000 psia. The total pressure will be dependent on the particular catalyst system employed.

More specifically, the carbon monoxide partial pressure of the hydroformylation reaction in general may range from about 1 to about 360 psia, and preferably from about 3 to about 270 psia, while the hydrogen partial pressure in general may range from about 15 to about 480 psia, and preferably from about 30 to about 300 psia. In general, the molar ratio of carbon monoxide to gaseous hydrogen may range from about 100:1 or greater to about 1:100 or less, the preferred carbon monoxide to gaseous hydrogen molar ratio being from about 1:10 to about 10:1. In an embodiment, the carbon monoxide partial pressure of the alkadiene hydroformylation process of this invention may range from about 100 to about 1800 psia or greater, preferably from about 100 to about 1000 psia, and more preferably from about 200 to about 500 psia, while the hydrogen partial pressure may range from about 100 to about 1800 psia, preferably from about 100 to about 1000 psia, and more preferably from about 200 to about 500 psia. In general, for the alkadiene hydroformylation reaction, the molar ratio of carbon monoxide to gaseous hydrogen may range from about 0.8:1 to about 100:1 or greater, the preferred carbon monoxide to gaseous hydrogen molar ratio being from about 1:1 to about 10:1. In general, for the pentenal hydroformylation reaction, the molar ratio of carbon monoxide to gaseous hydrogen may range from about 100:1 to about 1:100, the preferred carbon monoxide to gaseous hydrogen molar ratio being from about 10:1 to about 1:10.

Carbon monoxide partial pressure should be sufficient for the hydroformylation reaction of an alkadiene to pentenal to occur at an acceptable rate, but not so extreme that certain derivatization reactions, e.g., hydroformylation and hydrogenation, occur. Hydrogen partial pressure must be sufficient for the hydroformylation reaction to occur at an acceptable rate, but not so high that hydrogenation of butadiene, hydrogenation of pentenal intermediates, or isomerization of pentenal intermediates to undesired isomers, occurs. The carbon monoxide and hydrogen partial pressures will be dependent in part on the particular catalyst system employed.

The hydroformylation reaction is also conducted at a pentenal partial pressure and/or carbon monoxide partial pressure sufficient to selectively produce the 1,6-hexanedials. However, the pentenal conversion may be complete or incomplete, and the partial pressure of carbon monoxide may be higher or lower than the partial pressure of hydrogen as described above.

Further, the hydroformylation process may be conducted at a reaction temperature from about −25° C. to about 200° C. In general, a hydroformylation reaction temperature of about 50° C. to about 120° C. is preferred for all types of olefinic starting materials. In general, for the alkadiene hydroformylation reaction, a hydroformylation reaction temperature of about 20° C. to about 200° C. may be employed, preferably from about 50° C. to about 150° C., and more preferably from about 65° C. to about 115° C. In general, for the pentenal hydroformylation reaction, a hydroformylation reaction temperature of about 0° C. to about 200° C. may be employed, preferably from about 25° C. to about 150° C., and more preferably from about 50° C. to about 125° C. The temperature must be sufficient for reaction to occur (which may vary with catalyst system employed), but not so high that ligand or catalyst decomposition occurs. At high temperatures (which may vary with catalyst system employed), isomerization of pentenal intermediates to undesired isomers may occur.

Of course, it is to be also understood that the hydroformylation reaction conditions employed will be governed by the type of aldehyde product desired.

The alkadiene hydroformylation reaction is conducted at an alkadiene partial pressure and/or carbon monoxide partial pressure sufficient to selectively produce the 1,6- hexanedials. In certain instances, it has been found that if the partial pressure of carbon monoxide in the step (a) reaction system is higher than the partial pressure of hydrogen, the partial pressure of pentenal intermediates to hydrogenated and bishydroformylated byproducts is suppressed. It is believed that these reactions are inhibited by carbon monoxide. It has also been found that when the step (a) reaction is conducted with incomplete partial pressure of butadiene, the partial pressure of pentenal intermediates to bishydroformylated byproducts is suppressed. In general, the alkadiene partial pressure can range from about 1 weight percent to about 99 weight percent, preferably from about 1 weight percent to about 75 weight percent, and more preferably from about 1 weight percent to about 50 weight percent, based on the total weight of alkadiene feed to the reaction. While not wishing to be bound to any particular theory, it is believed that butadiene preferentially complexes with the metal-ligand complex catalyst, acting as an inhibitor to the hydroformylation of the pentenal intermediates. The partial pressure of butadiene may be accomplished by short reaction time, low total pressure, low catalyst concentration, and/or low temperature. High butadiene concentrations are especially useful in the hydroformylation processes of this invention.

The pentenal hydroformylation reaction is also conducted at a pentenal partial pressure and/or carbon monoxide partial pressure sufficient to selectively produce the 1,6-hexanedials. However, in the pentenal hydroformylation reaction, the pentenal partial pressure may be complete or incomplete, and the partial pressure of carbon monoxide may be higher or lower than the partial pressure of hydrogen as described above.

To enable maximum levels of 3-pentenals and/or 4-pentenals and minimize 2-pentenals, it is desirable to maintain some alkadiene partial pressure or when the alkadiene conversion is complete, the carbon monoxide partial pressure should be sufficient to prevent or minimize derivatization, e.g., isomerization and/or hydrogenation, of substituted or unsubstituted 3-pentenals.

In a preferred embodiment, the alkadiene hydroformylation is conducted at an alkadiene partial pressure and/or a carbon monoxide partial pressure sufficient to prevent or minimize derivatization, e.g., isomerization and/or hydrogenation, of substituted or unsubstituted 3-pentenals. In a more preferred embodiment, the alkadiene, i.e., butadiene, hydroformylation is conducted at an alkadiene partial pressure of greater than 0 psi, preferably greater than 5 psi, and more preferably greater than 9 psi; and at a carbon monoxide partial pressure of greater than 0 psi, preferably greater than 25 psi, and more preferably greater than 100 psi.

The hydroformylation reaction is also conducted in the presence of water or an organic solvent for the metal-ligand complex catalyst and free ligand. Depending on the particular catalyst and reactants employed, suitable organic solvents include, for example, alcohols, alkanes, alkenes, alkynes, ethers, aldehydes, higher boiling aldehyde condensation byproducts, ketones, esters, amides, tertiary amines, aromatics and the like. Any suitable solvent which does not unduly adversely interfere with the intended hydroformylation reaction can be employed. Such solvents may include those commonly employed in known metal catalyzed hydroformylation reactions. Mixtures of one or more different solvents may be employed if desired. In general, with regard to the production of aldehydes, it is preferred to employ aldehyde compounds corresponding to the aldehyde products desired to be produced and/or higher boiling aldehyde liquid condensation byproducts as the main organic solvents as is common in the art. Such aldehyde condensation byproducts can also be preformed if desired and used accordingly. Illustrative preferred solvents employable in the production of aldehydes include ketones (e.g., acetone and methylethyl ketone), esters (e.g., ethyl acetate), hydrocarbons (e.g., toluene), nitrohydrocarbons (e.g., nitrobenzene), ethers (e.g., tetrahydrofuran (THF) and glyme), 1,4-butanediols and sulfolane. Suitable solvents are disclosed in U.S. Pat. No. 5,312,996. The amount of solvent employed is not critical and need only be that amount sufficient to solubilize the catalyst and free ligand of the hydroformylation reaction mixture to be treated. In general, the amount of solvent may range from about 5 percent by weight up to about 99 percent by weight or more based on the total weight of the hydroformylation reaction mixture starting material.

In an embodiment of the invention, the hydroformylation reaction mixture may consist of one or more liquid phases, e.g., a polar and a nonpolar phase. Such processes are often advantageous in, for example, separating products from catalyst and/or reactants by partitioning into either phase. In addition, product selectivities dependent upon solvent properties may be increased by carrying out the reaction in that solvent. An application of this technology is the aqueous-phase hydroformylation of olefins employing sulfonated phosphine ligands for the rhodium catalyst. A process carried out in aqueous solvent is particularly advantageous for the preparation of aldehydes because the products may be separated from the catalyst by extraction into an organic solvent. Alternatively, aldehydes, particularly pentenals and adipaldehyde, which tend to undergo self-condensation reactions, are expected to be stabilized in aqueous solution as the aldehyde hydrates.

As described herein, the phosphorus-containing ligand for the hydroformylation catalyst may contain any of a number of substituents, such as cationic or anionic substituents, which will render the catalyst soluble in a polar phase, e.g., water. Optionally, a phase-transfer catalyst may be added to the reaction mixture to facilitate transport of the catalyst, reactants, or products into the desired solvent phase. The structure of the ligand or the phase-transfer catalyst is not critical and will depend on the choice of conditions, reaction solvent, and desired products.

When the catalyst is present in a multiphasic system, the catalyst may be separated from the reactants and/or products by conventional methods such as extraction or decantation. The reaction mixture itself may consist of one or more phases; alternatively, the multiphasic system may be created at the end of the reaction by, for example, addition of a second solvent to separate the products from the catalyst. See, for example, U.S. Pat. No. 5,180,854, the disclosure of which is incorporated herein by reference.

In an embodiment of the process of this invention, an olefin can be hydroformylated along with an alkadiene or pentenal using the above-described metal-ligand complex catalysts. In such cases, an aldehyde derivative of the olefin is also produced along with the 1,6-hexanedials.

Mixtures of different olefinic starting materials can be employed, if desired, in the hydroformylation reactions. More preferably the hydroformylation reactions are especially useful for the production of alkenals, by hydroformylating alkadienes in the presence of alpha olefins containing from 2 to 30, preferably 4 to 20, carbon atoms, including isobutylene, and internal olefins containing from 4 to 20 carbon atoms as well as starting material mixtures of such alpha olefins and internal olefins. Commercial alpha olefins containing four or more carbon atoms may contain minor amounts of corresponding internal olefins and/or their corresponding saturated hydrocarbon and that such commercial olefins need not necessarily be purified from same prior to being hydroformylated.

Illustrative of other olefinic starting materials include alpha-olefins, internal olefins, 1,3-dienes, alkyl alkenoates, alkenyl alkanoates, alkenyl alkyl ethers, alkenols, alkenals, and the like, e.g., ethylene, propylene, 1-butene, 1-pentene, 1-hexene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-methylbutene, 2-pentene, 2-hexene, 3-hexane, 2-heptene, cyclohexene, propylene dimers, propylene trimers, propylene tetramers, piperylene, isoprene, 2-ethyl-1-hexene, 2-octene, styrene, 3-phenyl-1-propene, 1,4-hexadiene, 1,7-octadiene, 3-cyclohexyl-1-butene, allyl alcohol, allyl butyrate, hex-1-en-4-ol, oct-1-en-4-ol, vinyl acetate, allyl acetate, 3-butenyl acetate, vinyl propionate, allyl propionate, methyl methacrylate, vinyl ethyl ether, vinyl methyl ether, vinyl cyclohexene, allyl ethyl ether, methyl pentenoate, n-propyl-7-octenoate, pentenals, e.g., 2-pentenal, 3-pentenal and 4-pentenal; pentenols, e.g., 2-pentenol, 3-pentenol and 4-pentenol; 3-butenenitrile, 3-pentenenitrile, 5-hexenamide, 4-methyl styrene, 4-isopropyl styrene, 4-tert-butyl styrene, alpha-methyl styrene, 4-tert-butyl-alpha-methyl styrene, 1,3-diisopropenylbenzene, eugenol, iso-eugenol, safrole, iso-safrole, anethol, 4-allylanisole, indene, limonene, beta-pinene, dicyclopentadiene, cyclooctadiene, camphene, linalool, and the like. Other illustrative olefinic compounds may include, for example, p-isobutylstyrene, 2-vinyl-6-methoxynaphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl) styrene, 2-ethenyl-5-benzoylthiophene, 3-ethenylphenyl phenyl ether, propenylbenzene, isobutyl-4-propenylbenzene, phenyl vinyl ether and the like. Other olefinic compounds include substituted aryl ethylenes as described in U.S. Pat. No. 4,329,507, the disclosure of which is incorporated herein by reference.

As indicated above, it is generally preferred to carry out the hydroformylation process of this invention in a continuous manner. In general, continuous hydroformylation processes are well known in the art and may involve: (a) hydroformylating the olefinic starting material(s) with carbon monoxide and hydrogen in a liquid homogeneous reaction mixture comprising a solvent, the metal-ligand complex catalyst, and free ligand; (b) maintaining reaction temperature and pressure conditions favorable to the hydroformylation of the olefinic starting material(s); (c) supplying make-up quantities of the olefinic starting material(s), carbon monoxide and hydrogen to the reaction medium as those reactants are used up; and (d) recovering the desired aldehyde hydroformylation product(s) in any manner desired. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass through without recycling the unreacted olefinic starting material(s). However, it is generally desirable to employ a continuous process that involves either a liquid and/or gas recycle procedure. Such types of recycle procedure are well known in the art and may involve the liquid recycling of the metal-ligand complex catalyst solution separated from the desired aldehyde reaction product(s), such as disclosed e.g., in U.S. Pat. No. 4,148,830 or a gas cycle procedure such as disclosed e.g., in U.S. Pat. No. 4,247,486, as well as a combination of both a liquid and gas recycle procedure if desired. The disclosures of said U.S. Pat. Nos. 4,148,830 and 4,247,486 are incorporated herein by reference thereto. The most preferred hydroformylation process of this invention comprises a continuous liquid catalyst recycle process.

Illustrative 1,6-hexanedials that can be prepared by the processes of this invention include 1,6-hexanedial (i.e., adipaldehyde) and substituted 1,6-hexanedials (e.g., 2-methyl-1,6-hexanedial and 3,4-dimethyl-1,6-hexanedial) and the like. Illustrative of suitable substituted and unsubstituted 1,6-hexanedials (including derivatives of 1,6-hexanedials) include those permissible substituted and unsubstituted 1,6-hexanedials which are described in Kirk-Othmer, Encyclopedia of Chemical Technology, Fourth Edition, 1996, the pertinent portions of which are incorporated herein by reference.

Illustrative substituted and unsubstituted alkenal intermediates that can be prepared by the processes of this invention include one or more of the following: cis-2-pentenal, trans-2-pentenal, cis-3-pentenal, trans-3-pentenal, and/or 4-pentenal, including mixtures comprising one or more alkenals. Illustrative of suitable substituted and unsubstituted alkenal intermediates (including derivatives of alkenal intermediates) include those permissible substituted and unsubstituted alkenals which are described in Kirk-Othmer, Encyclopedia of Chemical Technology, Fourth Edition, 1996, the pertinent portions of which are incorporated herein by reference.

As indicated above, the hydroformylation reactions may involve a liquid catalyst recycle procedure. Such liquid catalyst recycle procedures are known as seen disclosed, e.g., in U.S. Pat. Nos. 4,668,651; 4,774,361; 5,102,505 and 5,110,990. For instance, in such liquid catalyst recycle procedures it is common place to continuously or intermittently remove a portion of the liquid reaction product medium, containing, e.g., the aldehyde product, the solubilized metal-ligand complex catalyst, free ligand, and organic solvent, as well as byproducts produced in situ by the hydroformylation, e.g., aldehyde condensation byproducts etc., and unreacted olefinic starting material, carbon monoxide and hydrogen (syn gas) dissolved in said medium, from the hydroformylation reactor, to a distillation zone, e.g., a vaporizer/separator wherein the desired aldehyde product is distilled in one or more stages under normal, reduced or elevated pressure, as appropriate, and separated from the liquid medium. The vaporized or distilled desired aldehyde product so separated may then be condensed and recovered in any conventional manner as discussed above. The remaining non-volatilized liquid residue which contains metal-ligand complex catalyst, solvent, free ligand and usually some undistilled aldehyde product is then recycled back, with or with out further treatment as desired, along with whatever by-product and non-volatilized gaseous reactants that might still also be dissolved in said recycled liquid residue, in any conventional manner desired, to the hydroformylation reactor, such as disclosed e.g., in the above-mentioned patents. Moreover the reactant gases so removed by such distillation from the vaporizer may also be recycled back to the reactor if desired.

In an embodiment of this invention, the aldehyde mixtures may be separated from the other components of the crude reaction mixtures in which the aldehyde mixtures are produced by any suitable method. Suitable separation methods include, for example, solvent extraction, crystallization, distillation, vaporization, wiped film evaporation, falling film evaporation and the like. It may be desired to remove the aldehyde products from the crude reaction mixture as they are formed through the use of trapping agents as described in published Patent Cooperation Treaty Patent Application WO 88/08835. A preferred method for separating the aldehyde mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, both incorporated herein by reference.

As indicated above, at the conclusion of (or during) the process of this invention, the desired 1,6-hexanedials may be recovered from the reaction mixtures used in the process of this invention. For example, the recovery techniques disclosed in U.S. Pat. Nos. 4,148,830 and 4,247,486 can be used. For instance, in a continuous liquid catalyst recycle process the portion of the liquid reaction mixture (containing 1,6-hexanedial product, catalyst, etc.) removed from the reactor can be passed to a vaporizer/separator wherein the desired 1,6-hexanedial product can be separated via distillation, in one or more stages, under normal, reduced or elevated pressure, from the liquid reaction solution, condensed and collected in a product receiver, and further purified if desired. The remaining non-volatilized catalyst containing liquid reaction mixture may then be recycled back to the reactor as may if desired any other volatile materials, e.g., unreacted olefin, together with any hydrogen and carbon monoxide dissolved in the liquid reaction after separation thereof from the condensed 1,6-hexanedial product, e.g., by distillation in any conventional manner. It is generally desirable to employ an organophosphorus ligand whose molecular weight exceeds that of the higher boiling aldehyde oligomer byproducts corresponding to the 1,6-hexanedials being produced in the hydroformylation process. Another suitable recovery technique is solvent extraction or crystallization. In general, it is preferred to separate the desired 1,6-hexanedials from the catalyst-containing reaction mixture under reduced pressure and at low temperatures so as to avoid possible degradation of the organophosphorus ligand and reaction products. When an alpha-mono-olefin reactant is also employed, the aldehyde derivative thereof can also be separated by the above methods.

More particularly, distillation and separation of the desired aldehyde product (e.g., 1,6-hexanedial) from the metal-ligand complex catalyst containing product solution may take place at any suitable temperature desired. In general, it is recommended that such distillation take place at relatively low temperatures, such as below 150° C., and more preferably at a temperature in the range of from about 50° C. to about 130° C. It is also generally recommended that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g. $C_7$ or greater) are involved. For instance, a common practice subjects the liquid reaction product medium removed from the hydroformylation reactor to a reduced pressure to volatilize a substantial portion of the unreacted gases dissolved in the liquid medium which contains a much lower synthesis gas concentration than was present in the hydroformylation, the distills the reaction medium in a distillation zone, e.g., vaporizer/separator, where the desired aldehyde product is distilled. In general, distillation pressures ranging from vacuum pressures on up to total gas pressure of about 50 psig should be sufficient for most purposes.

Particularly when conducting the process of this invention in a continuous liquid recycle mode employing an organophosphite ligand, undesirable acidic byproducts (e.g., a hydroxy alkyl phosphonic acid) may result due to reaction of the organophosphite ligand and the aldehydes over the course of the process. The formation of such byproducts undesirably lowers the concentration of the ligand. Such acids are often insoluble in the reaction mixture and such insolubility can lead to precipitation of an undesirable gelatinous byproduct and may also promote the autocatalytic formation of further acidic byproducts. The organopolyphosphite ligands used in the process of this invention have good stability against the formation of such acids. However, if this problem does occur, the liquid reaction effluent stream of a continuous liquid recycle process may be passed, prior to (or more preferably after) separation of the desired alkenal, preferably pentenal, product therefrom, through any suitable weakly basic anion exchange resin, such as a bed of amine Amberlyst® resin, e.g., Amberlyst® A-21, and the like, to remove some or all of the undesirable acidic byproducts prior to its reincorporation into the hydroformylation reactor. If desired, more than one such basic anion exchange resin bed, e.g. a series of such beds, may be employed and any such bed may be easily removed and/or replaced as required or desired. Alternatively if desired, any part or all of the acid-contaminated catalyst recycle stream may be periodically removed from the continuous recycle operation and the contaminated liquid so removed treated in the same fashion as outlined above, to eliminate or reduce the amount of acidic by-product prior to reusing the catalyst containing liquid in the hydroformylation process. Likewise, any other suitable method for removing such acidic byproducts from the hydroformylation process of this invention may be employed herein if desired such as by extraction of the acid with a weak base (e.g., sodium bicarbonate).

The processes useful in this invention may involve improving the catalyst stability of any organic solubilized rhodium-organopolyphosphite complex catalyzed, liquid recycle hydroformylation process directed to producing aldehydes from olefinic unsaturated compounds which may experience deactivation of the catalyst due to recovery of the aldehyde product by vaporization separation from a reaction product solution containing the organic solubilized rhodium-organopolyphosphite complex catalyst and aldehyde product, the improvement comprising carrying out said vaporization separation in the presence of a heterocyclic nitrogen compound. See, for example, copending U.S. patent application Ser. No. 08/756,789, filed Nov. 26, 1996, the disclosure of which is incorporated herein by reference.

The processes useful in this invention may involve improving the hydrolytic stability of the organophosphite ligand and thus catalyst stability of any organic solubilized rhodium-organophosphite ligand complex catalyzed hydroformylation process directed to producing aldehydes from olefinic unsaturated compounds, the improvement comprising treating at least a portion of an organic solubilized rhodium-organophosphite ligand complex catalyst solution derived from said process and which also contains phosphorus acidic compounds formed during the hydroformylation process, with an aqueous buffer solution in order to neutralize and remove at least some amount of said phosphorus acidic compounds from said catalyst solution, and then returning the treated catalyst solution to the hydroformylation reactor. See, for example, copending U.S. patent application Ser. Nos. 08/756,501 and 08/753,505, both filed Nov. 26, 1996, the disclosures of which are incorporated herein by reference.

In an embodiment of this invention, deactivation of metal-organopolyphosphorus ligand complex catalysts caused by an inhibiting or poisoning organomonophosphorous compound can be reversed or at least minimized by carrying out hydroformylation processes in a reaction region where the hydroformylation reaction rate is of a negative or inverse order in carbon monoxide and optionally at one or more of the following conditions: at a temperature such that the temperature difference between reaction product fluid temperature and inlet coolant temperature is sufficient to prevent and/or lessen cycling of carbon monoxide partial pressure, hydrogen partial pressure, total reaction pressure, hydroformylation reaction rate and/or temperature during said hydroformylation process; at a carbon monoxide conversion sufficient to prevent and/or lessen cycling of carbon monoxide partial pressure, hydrogen partial pressure, total reaction pressure, hydroformylation reaction rate and/or temperature during said hydroformylation process; at a hydrogen conversion sufficient to prevent and/or lessen cycling of carbon monoxide partial pressure, hydrogen partial pressure, total reaction pressure, hydroformylation reaction rate and/or temperature during said hydroformylation process; and at an olefinic unsaturated compound conversion sufficient to prevent and/or lessen cycling of carbon monoxide partial pressure, hydrogen partial pressure, total reaction pressure, hydroformylation reaction rate and/or temperature during said hydroformylation process. See, for example, copending U.S. patent application Ser. No. 08/756,499, filed Nov. 26, 1996, the disclosure of which is incorporated herein by reference.

In a preferred embodiment of this invention for producing one or more substituted or unsubstituted 1,6-hexanedials, the overall hydroformylation reaction generally proceeds in two stages. In the first stage, the substituted or unsubstituted alkadiene is converted to one or more substituted or unsubstituted unsaturated aldehydes (i.e., a 3-pentenal and/or 4-pentenal). In the second stage, the 3-pentenal isomerizes to 4-pentenal which can be readily further hydroformylated to a 1,6-hexanedial, e.g., adipaldehyde, and the 4-pentenal initially produced also is hydroformylated to a 1,6-hexanedial, e.g., adipaldehyde. The 3-pentenal produced in the first stage is also capable of a side reaction, i.e., isomerization to a 2-pentenal. Such 2-pentenals are relatively inert to further hydroformylation but fairly readily hydrogenate to produce undesirable pentanals. In the case of the hydroformylation of butadiene itself, certain of these reactions are illustrated by the following scheme:

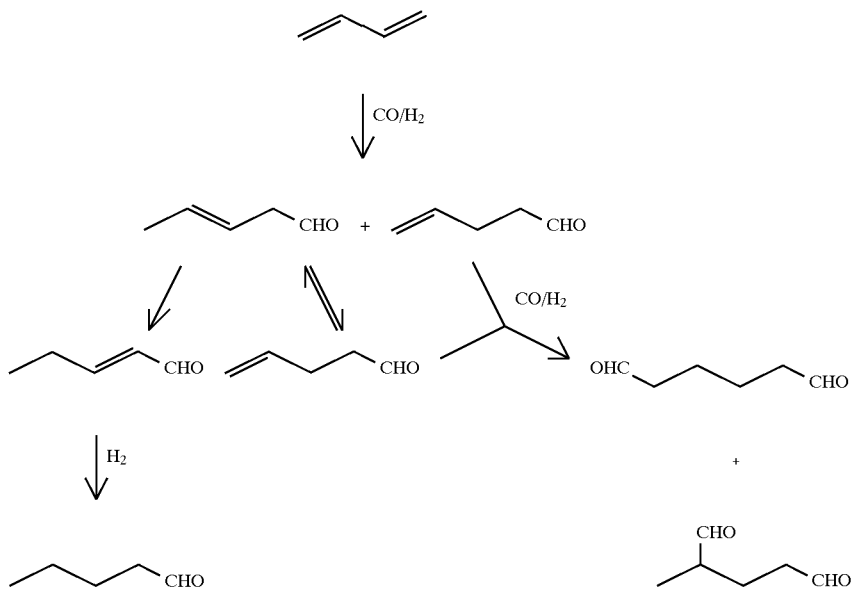

Another preferred embodiment of this invention relates to a process for producing one or more substituted or unsubstituted 1,6-hexanedials which comprises:
(a) subjecting one or more substituted or unsubstituted alkadienes, e.g., butadiene, or a mixture comprising one or more substituted or unsubstituted alkadienes to hydroformylation in the presence of a hydroformylation catalyst, e.g., a metal-organophosphorus ligand complex catalyst, and at an alkadiene partial pressure and/or a carbon monoxide partial pressure sufficient to produce one or more substituted or unsubstituted unsaturated aldehydes comprising 3-pentenals and/or 4-pentenal;
(b) optionally separating the 3-pentenals and/or 4-pentenal from the hydroformylation catalyst before any substantial amount of 2-pentenals form (e.g., before 10 weight percent, or preferably before 1 weight percent, of 2-pentenals form based on the total amount of 3-pentenals present); and
(c) subjecting said one or more unsaturated aldehydes comprising 3-pentenals and/or 4-pentenal to hydroformylation in the presence of a hydroformylation catalyst, e.g., a metal-organophosphorus ligand complex catalyst, to produce said one or more 1,6-hexanedials. The reaction conditions in steps (a) and (c) may be the same or different and the hydroformylation catalysts in steps (a) and (c) may be the same or different.

Yet another preferred embodiment of this invention relates to a process for producing one or more substituted or unsubstituted 1,6-hexanedials which comprises:
(a) subjecting one or more substituted or unsubstituted alkadienes, e.g., butadiene, or a mixture comprising one or more substituted or unsubstituted alkadienes to hydroformylation in the presence of a hydroformylation catalyst, e.g., a metal-organophosphorus ligand complex catalyst, and at an alkadiene partial pressure and/or carbon monoxide partial pressure sufficient to produce one or more substituted or unsubstituted unsaturated aldehydes comprising 2-pentenals, 3-pentenals and/or 4-pentenal;

(b) optionally separating the 2-pentenals, 3-pentenals and/or 4-pentenal from the hydroformylation catalyst; and (c) subjecting said one or more substituted or unsubstituted unsaturated aldehydes comprising 2-pentenals, 3-pentenals and/or 4-pentenal to hydroformylation in the presence of a hydroformylation catalyst, e.g., a metal-organophosphorus ligand complex catalyst, to produce said one or more substituted or unsubstituted 1,6-hexanedials. The reaction conditions in steps (a) and (c) may be the same or different and the hydroformylation catalysts in steps (a) and (c) may be the same or different.

Still another preferred embodiment of this invention relates to a process for producing one or more substituted or unsubstituted 1,6-hexanedials which comprises:

(a) subjecting one or more substituted or unsubstituted alkadienes, e.g., butadiene, or a mixture comprising one or more substituted or unsubstituted alkadienes to hydroformylation in the presence of a hydroformylation catalyst, e.g., a metal-organophosphorus ligand complex catalyst, and at an alkadiene partial pressure and/or a carbon monoxide partial pressure sufficient to produce one or more substituted or unsubstituted unsaturated aldehydes comprising 3-pentenals and/or 4-pentenal;

(b) optionally separating the 3-pentenals and/or 4-pentenal from the hydroformylation catalyst before any substantial amount of 2-pentenals form (e.g., before 10 weight percent, or preferably before 1 weight percent, of 2-pentenals form based on the total amount of 3-pentenals present);

(c) optionally subjecting the 3-pentenals and/or 4-pentenal to isomerization in the presence of a heterogeneous or homogeneous olefin isomerization catalyst to partially or completely isomerize the 3-pentenals to 4-pentenal; and (d) subjecting said one or more substituted or unsubstituted unsaturated aldehydes comprising 3-pentenals and/or 4-pentenal to hydroformylation in the presence of a hydroformylation catalyst, e.g., a metal-organophosphorus ligand complex catalyst, to produce said one or more substituted or unsubstituted 1,6-hexanedials. The reaction conditions in steps (a) and (d) may be the same or different and the hydroformylation catalysts in steps (a) and (d) may be the same or different.

Another preferred embodiment of this invention relates to a process for producing one or more substituted or unsubstituted 1,6-hexanedials which comprises:

(a) subjecting one or more substituted or unsubstituted alkadienes, e.g., butadiene, or a mixture comprising one or more substituted or unsubstituted alkadienes to hydroformylation in the presence of a hydroformylation catalyst, e.g., a metal-organophosphorus ligand complex catalyst, and at an alkadiene partial pressure and/or carbon monoxide partial pressure sufficient to produce one or more substituted or unsubstituted unsaturated aldehydes comprising 2-pentenals, 3-pentenals and/or 4-pentenal;

(b) optionally separating the 2-pentenals, 3-pentenals and/or 4-pentenal from the hydroformylation catalyst;

(c) optionally subjecting the 2-pentenals, 3-pentenals and/or 4-pentenal to isomerization in the presence of a heterogeneous or homogeneous olefin isomerization catalyst to partially or completely isomerize the 2-pentenals and/or 3-pentenals to 3-pentenals and/or 4-pentenal; and (d) subjecting said one or more substituted or unsubstituted unsaturated aldehydes comprising 2-pentenals, 3-pentenals and/or 4-pentenal to hydroformylation in the presence of a hydroformylation catalyst, e.g., a metal-organophosphorus ligand complex catalyst, to produce said one or more substituted or unsubstituted 1,6-hexanedials. The reaction conditions in steps (a) and (d) may be the same or different and the hydroformylation catalysts in steps (a) and (d) may be the same or different.

The olefin isomerization catalyst in step (c) may be any of a variety of homogeneous or heterogeneous transition metal-based catalysts (particularly Ni, Rh, Pd, Pt, Co, Ru, or Ir), or may be a heterogeneous or homogeneous acid catalyst (particularly any acidic zeolite, polymeric resin, or source of $H^+$, any of which may be modified with one or more transition metals). Such olefin isomerization catalysts are known in the art and the isomerization can be conducted by conventional procedures known in the art. As used herein, the term "isomerization" is contemplated to include, but not limited to, all permissible isomerization processes which involve converting one or more substituted or unsubstituted 2-pentenals and/or 3-pentenals or a mixture comprising one or more substituted or unsubstituted 2-pentenals and/or 3-pentenals to one or more substituted or unsubstituted 4-pentenals or a mixture comprising one or more substituted or unsubstituted 4-pentenals.

The undesirable isomerization of the 3-pentenals to form 2-pentenals can be avoided by converting the 3-pentenals to an acetal by reaction of the 3-pentenals with an alkanol, e.g., primary or secondary alcohols such as 2-dodecanol, isopropanol, cyclohexanol and 2,2-dimethylpropanol and monohydric alcohols such as methanol, ethanol, propanol, isopropanol, n-pentanol, 2-methylpropanol and n-butanol; a 1,2-diol, a 1,3-diol, or a 2,4-diol, or a polyol, preferably in the presence of an acetalization catalyst. Water is formed as a byproduct in the acetalization reaction and may undergo undesirable reaction with the ligand. Hence the water is preferably separated from the acetals. Suitable diols for use in forming the acetals of the 3-pentenals are ethylene glycol, 2,3-butanediol, 2,3-dimethyl-2,3-butanediol (pinacol) and 2,4-pentanediol and suitable acetalization catalysts are acidic compounds such as pyridinium tosylate, sulfuric acid, Amberlyst® resins, phosphoric acid and like. Such acetalization catalysts are known in the art and the acetalization can be conducted by conventional procedures known in the art. As used herein, the term "acetalization" is contemplated to include, but not limited to, all permissible acetalization processes which involve converting one or more substituted or unsubstituted 2-pentenals, 3-pentenals and/or 4-pentenal or a mixture comprising one or more substituted or unsubstituted 2-pentenals, 3-pentenals and/or 4-pentenal to one or more acetals of substituted or unsubstituted 2-pentenals, 3-pentenals and/or 4-pentenal or a mixture comprising one or more acetals of substituted or unsubstituted 2-pentenals, 3-pentenals and/or 4-pentenal.

The acetal can then be readily hydroformylated further to produce a monoacetal of the 1,6-hexanedial. The monoacetal can be readily converted to a 1,6-alkanedial by hydrolysis with an acid catalyst. Such acid catalysts are known in the art and the hydrolysis can be conducted by conventional procedures known in the art. As used herein, the term "hydrolysis" is contemplated to include, but not limited to, all permissible hydrolysis processes which involve converting one or more acetals of a substituted or unsubstituted 1,6-alkanedial or a mixture comprising one or more acetals of a substituted or unsubstituted 1,6-alkanedial to one or more substituted or unsubstituted 1,6-alkanedials or a mixture comprising one or more substituted or unsubstituted 1,6-alkanedials.

Yet another preferred process of this invention relates to a process for producing one or more substituted or unsubstituted 1,6-hexanedials which comprises:

(a) subjecting one or more substituted or unsubstituted alkadienes, e.g., butadiene, or a mixture comprising one or more substituted or unsubstituted alkadienes to hydroformylation in the presence of a hydroformylation catalyst, e.g., a metal-organophosphorus ligand complex catalyst, and at an alkadiene partial pressure and/or carbon monoxide partial pressure sufficient to produce one or more substituted or unsubstituted unsaturated aldehydes comprising 3-pentenals and/or 4-pentenal;

(b) optionally separating the 3-pentenals and/or 4-pentenal from the hydroformylation catalyst before any substantial amount of 2-pentenals form (e.g., before 10 weight percent, or preferably before 1 weight percent, of 2-pentenals form based on the total amount of 3-pentenals present);

(c) subjecting the 3-pentenals and/or 4-pentenal to acetalization optionally in the presence of an acetalization catalyst to produce one or more substituted or unsubstituted acetals of 3-pentenals and water;

(d) optionally separating said one or more substituted or unsubstituted acetals of 3-pentenals and/or 4-pentenal from the water;

(e) subjecting said one or more substituted or unsubstituted acetals of 3-pentenals and/or 4-pentenal to hydroformylation in the presence of a hydroformylation catalyst, e.g., a metal-organophosphorus ligand complex catalyst, to produce one or more substituted or unsubstituted monoacetals of 1,6-hexanedial; and (f) subjecting said one or more substituted or unsubstituted monoacetals of 1,6-hexanedial to hydrolysis in the presence of a hydrolysis catalyst to produce said one or more substituted or unsubstituted 1,6-hexanedials. The reaction conditions in steps (a) and (e) may be the same or different and the hydroformylation catalysts in steps (a) and (e) may be the same or different.

Still another preferred embodiment of this invention relates to a process for producing one or more substituted or unsubstituted 1,6-hexanedials which comprises:

(a) subjecting one or more substituted or unsubstituted alkadienes, e.g., butadiene, or a mixture comprising one or more substituted or unsubstituted alkadienes to hydroformylation in the presence of a hydroformylation catalyst, e.g., a metal-organophosphorus ligand complex catalyst, and at an alkadiene partial pressure and/or a carbon monoxide partial pressure sufficient to produce one or more substituted or unsubstituted unsaturated aldehydes comprising 2-pentenals, 3-pentenals and/or 4-pentenal;

(b) optionally separating the 2-pentenals, 3-pentenals and/or 4-pentenal from the hydroformylation catalyst;

(c) subjecting the 2-pentenals, 3-pentenals and/or 4-pentenal to acetalization optionally in the presence of an acetalization catalyst to produce one or more substituted or unsubstituted acetals of 3-pentenals and water;

(d) optionally separating said one or more substituted or unsubstituted acetals of 2-pentenals, 3-pentenals and/or 4-pentenal from the water;

(e) subjecting said one or more substituted or unsubstituted acetals of 2-pentenals, 3-pentenals and/or 4-pentenal to hydroformylation in the presence of a hydroformylation catalyst, e.g., a metal-organophosphorus ligand complex catalyst, to produce one or more substituted or unsubstituted monoacetals of 1,6-hexanedial; and (f) subjecting said one or more substituted or unsubstituted monoacetals of 1,6-hexanedial to hydrolysis in the presence of a hydrolysis catalyst to produce said one or more substituted or unsubstituted 1,6-hexanedials. The reaction conditions in steps (a) and (e) may be the same or different and the hydroformylation catalysts in steps (a) and (e) may be the same or different.

The above-described preferred process of this invention further increases partial pressure of the alkadiene to the 1,6-hexanedial by reducing the formation both of the 2-pentenals (which form by isomerization of the 3-pentenals) and of pentanals derived from such 2-pentenals. Conversions to about 85% by weight or greater of 1,6-hexanedial may be achieved by employing this preferred process.

When the processes of this invention are conducted in two stages (i.e., first producing 3-pentenals and/or 4-pentenal under one set of conditions and then producing a 1,6-hexanedial from the 3-pentenals and/or 4-pentenal (or the acetals) under another set of conditions), it is preferred to conduct the first stage at a temperature from 75° C. to 110° C. and at a total pressure from 250 psi to 1000 psi and to conduct the second stage at a temperature from 60° C. to 100° C. and at a pressure from 100 psi to 500 psi. The same or different metal-ligand complex catalyst can be used in both stages. The other conditions can be the same or different in both stages.

It is also possible to increase the alkadiene selectivity to the desired 1,6-hexanedial (e.g., to achieve about 45% by weight selectivity or higher) by conducting the first hydroformylation stage in the presence of a suitable diol (described above) to achieve acetalization along with hydroformylation so as to produce directly the acetal of 1,6-hexanedial. The acetal can then be further reacted as in steps (e) and (f) above to produce the desired 1,6-hexanedial. However, in such cases the organophosphorus ligand may undergo undesirable side reactions during the first stage with the water formed in the acetalization reaction.

The substituted and unsubstituted 1,6-hexanedial products (e.g., adipaldehyde) have a wide range of utilities that are well known in the art, e.g., they are useful as starting materials for the production of alcohols (e.g., 1,6-hexanediol) and acids (e.g., adipic acid) by known processes. The substituted and unsubstituted 1,6-hexanedials, e.g., adipaldehyde, are also useful as intermediates in the production of epsilon caprolactam, hexamethylenediamine, epsilon caprolactone, nylon 6 and nylon 66.

A process involving the reductive hydroformylation of one or more substituted or unsubstituted alkadienes to produce one or more substituted or unsubstituted alkenols is disclosed in copending U.S. patent application Ser. No. 08/842,666, filed on an even date herewith, the disclosure of which is incorporated herein by reference. Another process involving the production of one or more substituted or unsubstituted alkenals and/or alkenols by hydroformylation and/or hydroformylation/hydrogenation is disclosed in copending U.S. patent application Ser. No. 08/843,387, filed on an even date herewith, the disclosure of which is incorporated herein by reference.

Cyclization of 1,6-Hexanedials

The 1,6-hexanedials prepared according to the invention may undergo cyclization to epsilon caprolactone. The cyclization process involves converting one or more substituted or unsubstituted 1,6-hexanedials, e.g., adipaldehyde, or a reaction mixture comprising one or more substituted or unsubstituted 1,6-hexanedials to one or more substituted or unsubstituted epsilon caprolactones or a reaction mixture comprising one or more substituted or unsubstituted epsilon caprolactones. "Cyclization" includes all permissible cyclization processes which involve converting one or more substituted or unsubstituted 1,6-hexanedials, e.g., adipaldehyde, or a reaction mixture of such 1,6-hexanedials to one or more corresponding epsilon caprolactones or a reaction mixture. The term "epsilon caprolactone" includes all permissible substituted or unsubstituted epsilon caprolactones, e.g., epsilon caprolactone, which may be derived from substituted or unsubstituted 1,6-hexanedials, e.g., adipaldehyde, or a reaction mixture of such 1,6-hexanedials.

Illustrative of substituted and unsubstituted 1,6-hexanedials include, for example, adipaldehyde or its oligomers or its cyclic acetal or oligomers and its hydrates or acetals or oligomers, and the like. 1,6-Hexanedials useful in the cyclization process are known materials and can be prepared as described above or by a conventional method. Preferably, however, the 1,6-hexanedials are produced by a process of the invention, as described above. For example, adipaldehyde can be produced by the hydroformylation steps described above or by a conventional process. Reaction mixtures comprising 1,6-hexanedials may be useful herein. The amount of 1,6-hexanedials employed in the cyclization step is not narrowly critical and can be any amount sufficient to produce epsilon caprolactone, preferably in high selectivities. Preferably, the adipaldehyde concentration is low to promote cyclization.

The particular cyclization reaction conditions are not narrowly critical and can be any effective cyclization procedures sufficient to produce the epsilon caprolactone intermediate. The cyclization reaction can be conducted at a temperature of from about 0° C. to about 150° C. for a period of about 1 hour or less to about 4 hours or longer with the longer time being used at the lower temperature. Preferably the temperature ranges from about 20° C. to about 120° C. for a cyclization reaction time ranging form about 1 hour or less to about 2 hours or longer, and more preferably at about 50° C. to about 100° C. for a reaction time of about 1 hour or less.

The cyclization reaction can be conducted over a wide range of pressures ranging from about 1 psig to about 1000 psig. It is preferable to conduct the cyclization reaction at pressures of from about 15 psig to about 100 psig. The cyclization reaction is preferably effected in the liquid or vapor states or mixtures thereof.

The cyclization reaction can be conducted using catalysts known to promote aldehyde disproportionations in conventional amounts and such catalysts may be homogeneous or heterogeneous. Illustrative heterogeneous cyclization catalysts include, for example, chromium promoted with barium, manganese, copper, calcium, zinc, barium-promoted copper chromite, silver on alumina, molybdenum oxide on alumina, copper/zinc oxides either supported on alumina or bulk oxides, platinum/tin on alumina, copper/chromium/barium, cobalt on alumina/silica. Preferred heterogeneous cyclization catalysts include barium promoted copper chromite, and copper/zinc oxide on alumina. Illustrative homogeneous cyclization catalysts include, for example, aluminum alkoxides, phenoxides, or alkyls, zirconium alkoxides, the lanthanide metal compounds, particularly samarium, antimony alkoxides, iron alkoxides, rhodium or iridium or ruthenium phosphine and phosphite complexes. Preferred homogeneous cyclization catalysts include aluminum alkoxides, and rhodium or ruthenium phosphine or phosphite complexes. The specific catalyst used should be capable of transforming adipaldehyde to epsilon caprolactone in high yield under mild conditions. Appropriate ligands or promoters may be incorporated into such catalysts to modify catalyst activity, selectivity, lifetime or ease of operability. Such ligands and promoters are known materials and can be used in conventional amounts. The cyclization reaction may also proceed uncatalyzed, initiated by heating to an appropriate temperature, e.g., about 150° C. or so.

The amount of cyclization catalyst used is generally dependent on the particular cyclization catalyst employed and can range from about 0.01 weight percent or less to about 10 weight percent or greater of the total weight of the starting materials.

Such cyclization reactions may be performed in any appropriate solvent, under any appropriate atmosphere, or in the gas phase. Such solvents and atmospheres are chosen to allow the most desirable catalyst performance. For example, reactions may be performed under hydrogen gas in order to stabilize the catalyst from decomposition reactions to unproductive catalysts. Suitable solvents include ethers, esters, lactones (such as epsilon caprolactone), ketones, aliphatic or aromatic hydrocarbons, fluorocarbons, silicones, polyethers, chlorinated hydrocarbons and the like.

Illustrative epsilon caprolactones that can be prepared by the processes of this invention include epsilon caprolactone and substituted epsilon caprolactones (e.g., alpha, beta, gamma and delta substituted epsilon caprolactones). Illustrative of suitable substituted and unsubstituted epsilon caprolactones (including derivatives of epsilon caprolactones) include those permissible substituted or unsubstituted epsilon caprolactones which are described in Kirk-Othmer, Encyclopedia of Chemical Technology, Fourth Edition, 1996, the pertinent portions of which are incorporated herein by reference.

The substituted and unsubstituted epsilon caprolactones produced by the cyclization step of this invention can be separated by conventional techniques such as distillation, extraction, precipitation, crystallization, membrane separation or other suitable means. For example, a crude reaction product can be subjected to a distillation-separation at atmospheric or reduced pressure through a packed distillation column. Reactive distillation may be useful in conducting the cyclization reaction step. Subsequent amination of the cyclization reaction mixtures may be conducted without the need to separate the epsilon caprolactone from the other components of the crude reaction mixtures.

The processes of this invention may be carried out using, for example, a fixed bed reactor, a fluid bed reactor, or a slurry reactor. The optimum size and shape of the catalysts will depend on the type of reactor used. In general, for fluid bed reactors, a small, spherical catalyst particle is preferred for easy fluidization. With fixed bed reactors, larger catalyst particles are preferred so the back pressure within the reactor is kept reasonably low.

The processes of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials. When complete partial pressure is not desired or not obtainable, the starting materials can be separated from the product, for example by distillation, and the starting materials then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The processes of this invention may be conducted in one or more steps or stages. The exact number of reaction steps or stages will be governed by the best compromise between achieving high catalyst selectivity, activity, lifetime and ease of operability, as well as the intrinsic reactivity of the starting materials in question and the stability of the starting materials and the desired reaction product to the reaction conditions.

In an embodiment, the hydroformylation processes useful in this invention may be carried out in a multistaged reactor such as described, for example, in copending U.S. patent application Ser. No.08/757,743, filed on Nov. 26, 1996, the disclosure of which is incorporated herein by reference. Such multistaged reactors can be designed with internal, physical barriers that create more than one theoretical reactive stage per vessel. In effect, it is like having a number of reactors inside a single continuous stirred tank reactor vessel. Multiple reactive stages within a single vessel is a cost effective way of using the reactor vessel volume. It significantly reduces the number of vessels that otherwise would be required to achieve the same results. Fewer vessels reduces the overall capital required and maintenance concerns with separate vessels and agitators.

The substituted and unsubstituted 1,6-hexanedials produced by the processes of this invention can undergo further reaction(s) to afford desired derivatives thereof. Such permissible derivatization reactions can be carried out in accordance with conventional procedures known in the art. Illustrative derivatization reactions include, for example, hydrogenation, hydroformylation, esterification, etherification, amination, cyclization, acetalization, alkylation, dehydrogenation, reduction, acylation, condensation, oxidation, silylation and the like, including permissible combinations thereof. Preferred derivatization reactions and derivatives of 1,6-hexanedials include, for example, reductive amination to give hexamethylenediamine, oxidation to give adipic acid, cyclization to give epsilon caprolactone, cyclization and amination to give epsilon caprolactam, cyclization and amination to give an imino ether and further isomerization to give epsilon caprolactam, and hydrogenation or reduction to give 1,6-hexanediols. This invention is not intended to be limited in any manner by the permissible derivatization reactions or permissible derivatives of substituted and unsubstituted 1,6-hexanedials.

The substituted and unsubstituted epsilon caprolactones (and/or hydrates and/or esters) that may be produced by the processes of this invention can undergo further reaction(s) to afford desired derivatives thereof. Such permissible derivatization reactions can be carried out in accordance with conventional procedures known in the art. Illustrative derivatization reactions include, for example, hydrogenation, esterification, polymerization, copolymerization, etherification, amination, alkylation, dehydrogenation, reduction, acylation, cyclization, hydration, neutralization, condensation, carboxylation, carbonylation, oxidation, silylation and the like, including permissible combinations thereof. A preferred derivatization reaction and derivative of epsilon caprolactone includes, for example, amination to give epsilon caprolactam. This invention is not intended to be limited in any manner by the permissible derivatization reactions or permissible derivatives of substituted and unsubstituted epsilon caprolactones and/or hydrates and/or esters.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds which can be substituted or unsubstituted.

The term "substituted" is contemplated to include all permissible substituents of organic compounds unless otherwise indicated. In a broad aspect, the permissible substituents include acyclic (with or without heteroatoms) and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

For purposes of this invention, the chemical elements are identified in accordance with the Periodic Table of the Elements reproduced in "Basic Inorganic Chemistry" by F. Albert Cotton, Geoffrey Wilkinson and Paul L. Gaus, published by John Wiley and Sons, Inc., 3rd Edition, 1995.

The following examples are provided to further illustrate this invention.

EXAMPLE 1

A catalyst solution consisting of 0.019 grams of rhodium dicarbonyl acetylacetonate (300 parts per million rhodium), 0.31 grams of Ligand F identified above (5:1 ligand to rhodium ratio), and 25 milliliters of tetrahydrofuran was charged to a 100 milliliter Parr reactor. Butadiene (1.5 milliliters) was charged to the reactor as a liquid under pressure. The reaction was heated to 95° C. and pressurized to 250 psig with 4:1 carbon monoxide:hydrogen. After one hour the solution was analyzed by gas chromatography to determine product composition. Butadiene was 37% by weight converted. The products consisted of 75% by weight 3-pentenals, 2% by weight 2-pentenals, 6% by weight 4-pentenal, 2% by weight valeraldehyde, and 5% by weight adipaldehyde.

EXAMPLE 2

A catalyst solution consisting of 0.019 grams of rhodium dicarbonyl acetylacetonate (300 parts per million rhodium), 0.31 grams of Ligand F identified above (5:1 ligand to rhodium ratio), and 25 milliliters of diglyme was charged to a 100 milliliter Parr reactor. Butadiene (7 milliliters) was charged to the reactor as a liquid under pressure. The reaction was heated to 95° C. and pressurized to 1000 psig with 4:1 carbon monoxide:hydrogen. The solution was analyzed by gas chromatography at intervals to determine product composition. The results are shown in Table A below.

TABLE A

| Reaction Time (Minutes) | 3-Pentenals (Wt. %) | 4-Pentenal (Wt. %) | 2-Pentenals (Wt. %) | Valeraldehyde (Wt. %) | Branched Dialdehyde (Wt. %) | Adipaldehyde (Wt. %) |
| --- | --- | --- | --- | --- | --- | --- |
| 10 | 75 | 11 | 1 | | 2 | 8 |
| 30 | 74 | 8 | 3 | 1 | 3 | 10 |
| 60 | 68 | 3 | 5 | 2 | 5 | 15 |
| 90 | 55 | | 7 | 9 | 8 | 19 |
| 120 | 36 | | 6 | 24 | 11 | 22 |

EXAMPLE 3

A catalyst solution consisting of 0.136 grams of rhodium dicarbonyl acetylacetonate (300 parts per million rhodium), 3 grams of Ligand F identified above (3.6:1 ligand to rhodium ratio), and 150 milliliters of tetrahydrofuran was charged to a 300 milliliter Parr autoclave. Butadiene (100 milliliters) was charged as a liquid under pressure. The reaction was heated to 95° C. and pressurized to 800 psi with 4:1 carbon monoxide:hydrogen. The reaction was periodically repressurized to 900 psi with syngas (1:1 carbon monoxide:hydrogen) to compensate for that absorbed by the solution. After 4 hours, the mixture was analyzed by gas chromatography to determine the product composition. The products consisted of 80% by weight pentenals, 11% by weight valeraldehyde, and 4% by weight adipaldehyde.

EXAMPLE 4

A catalyst solution consisting of 0.012 grams of rhodium dicarbonyl acetylacetonate (200 parts per million rhodium), 0.47 grams of Ligand E identified above (12:1 ligand to rhodium ratio), and 15 milliliters of tetrahydrofuran was charged to a 100 milliliter Parr reactor. Butadiene (2 milliliters) was charged to the reactor as a liquid under pressure. The reaction was heated to 95° C. and pressurized to 500 psig with 1:1 carbon monoxide:hydrogen. The reaction rate was determined by monitoring the rate of syngas (1:1 carbon monoxide:hydrogen) consumption. The rate of reaction was found to be 0.4 mol/1-hr. After two hours of reaction the solution was analyzed by gas chromatography to determine product composition. Butadiene was 95% by weight converted. The products consisted of 75% by weight 3-pentenals, 3% by weight 4-pentenal, 5% by weight 2-pentenals, 7% by weight valeraldehyde, 1% by weight branched dialdehyde, and 9% by weight adipaldehyde.

EXAMPLE 5

A catalyst solution consisting of 0.012 grams of rhodium dicarbonyl acetylacetonate (200 parts per million rhodium), 0.47 grams of Ligand D identified above (14:1 ligand to rhodium ratio), and 15 milliliters of tetrahydrofuran was charged to a 100 milliliter Parr reactor. Butadiene (2 milliliters) was charged to the reactor as a liquid under pressure. The reaction was heated to 95° C. and pressurized to 500 psig with 1:1 carbon monoxide:hydrogen. The reaction rate was determined by monitoring the rate of syngas (1:1 carbon monoxide:hydrogen) consumption. The rate of reaction was found to be 1.2 mol/1-hr. After two hours of reaction the solution was analyzed by gas chromatography to determine product composition. Butadiene was 68% by weight converted. The products consisted of 70% by weight 3-pentenals, 8% by weight 4-pentenal, 8% by weight 2-pentenals, 8% by weight valeraldehyde, 1% by weight branched dialdehyde, and 5% by weight adipaldehyde.

EXAMPLE 6

A catalyst solution consisting of 0.019 grams of rhodium dicarbonyl acetylacetonate (300 parts per million rhodium), 0.42 grams of the ligand depicted below (6:1 ligand to rhodium ratio), 2.29 grams of N-methypyrrolidinone (as an internal standard) and 25 milliliters of tetrahydrofuran was charged to a 100 milliliter Parr reactor. Butadiene (3 milliliters) was charged to the reactor as a liquid under pressure. The reaction was heated to 95° C. and pressurized to 500 psig with 1:1 carbon monoxide:hydrogen. After two hours of reaction the solution was analyzed by gas chromatography to determine product composition. Butadiene was 33% by weight converted. The products consisted of 87% by weight 3-pentenals, 3% by weight 2-pentenals, 4% by weight 4-pentenal, and 7% by weight valeraldehyde.

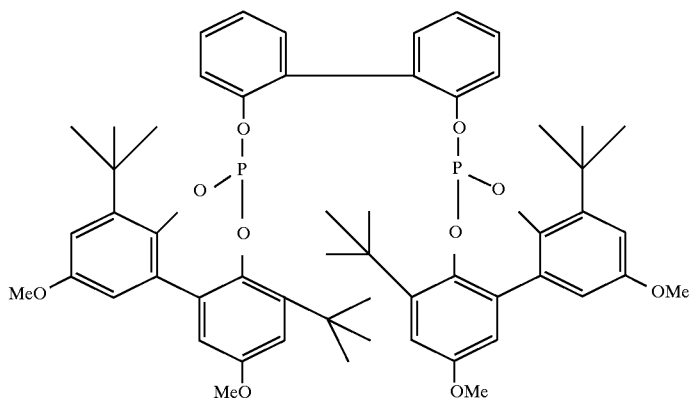

EXAMPLE 7

A catalyst solution consisting of 0.019 grams of rhodium dicarbonyl acetylacetonate (300 parts per million rhodium), 0.88 grams of the ligand depicted below (10–15:1 ligand to rhodium ratio), 2.19 grams of N-methylpyrrolidinone (as an internal standard) and 25 milliliters of tetrahydrofuran was charged to a 100 milliliter Parr reactor. Butadiene (3 milliliters) was charged to the reactor as a liquid under pressure. The reaction was heated to 95° C. and pressurized to 500 psig with 1:1 carbon monoxide:hydrogen. After two hours of reaction the solution was analyzed by gas chromatography to determine product composition. Butadiene was 33% by weight converted. The products consisted of 80% by weight 3-pentenals, 8% by weight 4-pentenal, 4% by weight 2-pentenals, and 8% by weight valeraldehyde.

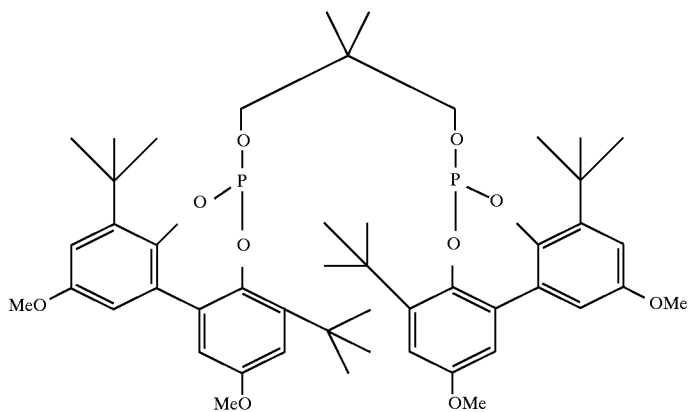

EXAMPLE 8

A catalyst solution consisting of 0.019 grams of rhodium dicarbonyl acetylacetonate (300 parts per million rhodium), 0.09 grams of the ligand depicted below (1.5:1 ligand to rhodium ratio), and 25 milliliters of tetrahydrofuran was charged to a 100 milliliter Parr reactor. Butadiene (1 milliliter) was charged to the reactor as a liquid under pressure. The reaction was heated to 95° C. and pressurized to 500 psig with 4:1 carbon monoxide:hydrogen. After one hour the solution was analyzed by gas chromatography to determine product composition. Butadiene was 51% by weight converted. The products consisted of 79% by weight 3-pentenals, 12% by weight 4-pentenal, and 5% by weight butenes.

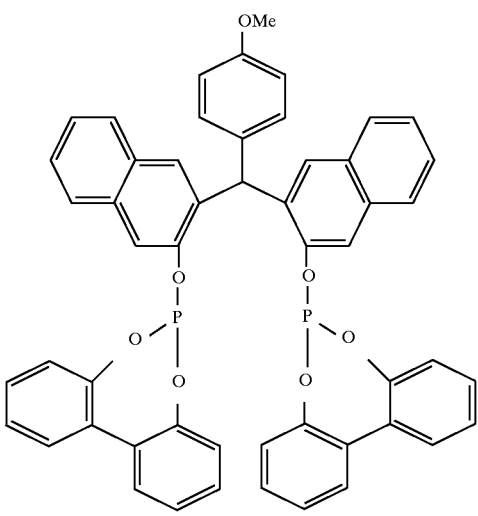

EXAMPLE 9

A catalyst solution consisting of 0.016 grams of rhodium dicarbonyl acetylacetonate and 2.089 grams of Ligand F identified above (3.6:1 ligand to rhodium ratio) and 160 milliliters of tetraglyme was charged to a 300 milliliter Parr autoclave. Butadiene (35 milliliters) was charged as a liquid under pressure. The reaction was heated to 95° C. and pressurized to 900 psi with 4:1 carbon monoxide:hydrogen. The reaction was periodically repressurized to 900 psi with syngas (1:1 carbon monoxide:hydrogen) to compensate for that absorbed by the solution. After 2.5 hours, the reactor was cooled and recharged with 35 milliliters of butadiene and the reaction repeated. A total of three 35 milliliter butadiene charges were reacted, in order to provide enough material for distillation. The mixture was analyzed by gas chromatography to determine the product composition. The hydroformylation products consisted of 53% by weight pentenals, 27% by weight valeraldehyde, and 12% by weight adipaldehyde. The product mixture was distilled at 260 mm Hg through a 25-tray Oldershaw column. The best distillation cuts, collected at a kettle temperature of 225° C., consisted of 77% by weight pentenals.

EXAMPLE 10

A catalyst solution consisting of 0.019 grams of rhodium dicarbonyl acetylacetonate (300 parts per million rhodium), 0.18 grams of triphenylphosphine ligand (10:1 ligand to rhodium ratio), and 25 milliliters of tetrahydrofuran was charged to a 100 milliliter Parr reactor. Butadiene (1 milliliter) was charged to the reactor as a liquid under pressure. The reaction was heated to 95° C. and pressurized to 500 psig with 1:1 carbon monoxide:hydrogen. After one hour the solution was analyzed by gas chromatography to determine product composition. Butadiene was approximately 60% by weight converted. The products consisted of 82% by weight 3-pentenals, 9% by weight 4-pentenal, 5% by weight valeraldehyde, and 4% by weight butenes. After two hours reaction time, the products consisted of 69% by weight 3-pentenals, 3% by weight 4-pentenal, 12% by weight valeraldehyde, 5% by weight adipaldehyde, 4% by weight methylglutaraldehyde, 3% by weight butenes, and 2% by weight 2-methylbutyraldehyde.

EXAMPLE 11

A catalyst solution consisting of 0.032 grams of rhodium dicarbonyl acetylacetonate (500 parts per million rhodium), 0.12 grams of tris(2-cyanoethyl)phosphine ligand (5:1 ligand to rhodium ratio), and 25 milliliters of tetrahydrofuran was charged to a 100 milliliter Parr reactor. Butadiene (3 milliliters) was charged to the reactor as a liquid under pressure. The reaction was heated to 110° C. and pressurized to 1000 psig with 1:1 carbon monoxide:hydrogen. After two hours of reaction the solution was analyzed by gas chromatography to determine product composition. Butadiene was approximately 68% by weight converted. The products consisted of 54% by weight 3-pentenals, 5% by weight 4-pentenal, 3% by weight 2-pentenals, 27% by weight valeraldehyde, and 7% by weight 2-methylbutyraldehyde.

EXAMPLE 12

A catalyst solution consisting of 0.019 grams of rhodium dicarbonyl acetylacetonate (300 parts per million rhodium), 0.20 grams of diphenyl(o-methoxyphenyl)phosphine ligand (10:1 ligand to rhodium ratio), and 25 milliliters of tetrahydrofuran was charged to a 100 milliliter Parr reactor. Butadiene (3 milliliters) was charged to the reactor as a liquid under pressure. The reaction was heated to 95° C. and pressurized to 500 psig with 1:1 carbon monoxide:hydrogen. After one hour the solution was analyzed by gas chromatography to determine product composition. Butadiene was approximately 50% by weight converted. The products consisted of 74% by weight 3-pentenals, 10% by weight 4-pentenal, 6% by weight valeraldehyde, and 8% by weight butenes.

EXAMPLE 13

A catalyst solution consisting of 0.019 grams of rhodium dicarbonyl acetylacetonate (300 parts per million rhodium), 0.24 grams of bis(diphenylphosphino)propane ligand (8:1 ligand to rhodium ratio), and 25 milliliters of tetrahydrofuran was charged to a 100 milliliter Parr reactor. Butadiene (3 milliliters) was charged to the reactor as a liquid under pressure. The reaction was heated to 95° C. and pressurized to 500 psig with 1:1 carbon monoxide:hydrogen. After two hours of reaction the solution was analyzed by gas chromatography to determine product composition. Butadiene was 50% by weight converted. The products consisted of only C5 aldehydes, with no dialdehyde present.

EXAMPLE 14

A catalyst solution consisting of 0.018 grams of rhodium dicarbonyl acetylacetonate (300 parts per million rhodium), 0.16 grams of isopropyldiphenylphosphine ligand (5:1 ligand to rhodium ratio), and 25 milliliters of tetrahydrofuran was charged to a 100 milliliter Parr reactor. Butadiene (1 milliliter) was charged to the reactor as a liquid under pressure. The reaction was heated to 95° C. and pressurized to 500 psig with 1:1 carbon monoxide:hydrogen. After two hours of reaction the solution was analyzed by gas chromatography to determine product composition. Butadiene was approximately 46% by weight converted. The products consisted of 79% by weight 3-pentenals, 9% by weight 4-pentenal, 5% by weight valeraldehyde, and 5% by weight butenes.

EXAMPLE 15

A catalyst solution consisting of 0.018 grams of rhodium dicarbonyl acetylacetonate (300 parts per million rhodium), 0.08 grams of bis(diphenylphosphino)ferrocene ligand (2:1 ligand to rhodium ratio), and 25 milliliters of tetrahydrofuran was charged to a 100 milliliter Parr reactor. Butadiene (1 milliliter) was charged to the reactor as a liquid under pressure. The reaction was heated to 75° C. and pressurized to 1000 psig with 10:1 carbon monoxide:hydrogen. After two hours of reaction the solution was analyzed by gas chromatography to determine product composition. Butadiene was approximately 54% by weight converted. The products consisted of 74% by weight 3-pentenals, and 25% by weight 4-pentenal.

EXAMPLE 16

A catalyst solution consisting of 0.019 grams of rhodium dicarbonyl acetylacetonate (300 parts per million rhodium), 0.31 grams of Ligand F (5:1 ligand to rhodium ratio), 10 microliters of trimethylphosphine ligand (2:1 ligand to rhodium ratio), and 25 milliliters of toluene was charged to a 100 milliliter Parr reactor. Butadiene (3 milliliters) was charged to the reactor as a liquid under pressure. The reaction was heated to 110° C. and pressurized to 1000 psig with 1:1 carbon monoxide:hydrogen. After two hours the solution was analyzed by gas chromatography to determine product composition. Butadiene was 80% by weight converted. The products consisted of 53% by weight 3-pentenals, 13% by weight 2-pentenals, 4% by weight 4-pentenal, 8% by weight valeraldehyde, 8% by weight adipaldehyde, and 7% by weight butenes.

EXAMPLE 17

A catalyst solution consisting of 0.019 grams of rhodium dicarbonyl acetylacetonate (300 parts per million rhodium), 0.12 grams of Ligand F identified above (2:1 ligand to rhodium ratio), 0.09 grams of tris(p-tolyl)phosphine ligand (4:1 ligand to rhodium ratio), and 25 milliliters of tetrahydrofuran was charged to a 100 milliliter Parr reactor. Butadiene (3 milliliters) was charged to the reactor as a liquid under pressure. The reaction was heated to 95° C. and pressurized to 500 psig with 1:1 carbon monoxide:hydrogen. After two hours the solution was analyzed by gas chromatography to determine product composition. Butadiene was 80% by weight converted. The products consisted of 51% by weight 3-pentenals, 5% by weight 2-pentenals, 26% by weight valeraldehyde, and 15% by weight adipaldehyde.

EXAMPLE 18

A catalyst solution consisting of 0.05 grams of (bicyclo [2.2.1]hepta-2,5-diene)[1,1'-bis(diphenylphosphino) ferrocene] rhodium(I)perchlorate (250 parts per million rhodium) in 25 milliliters of tetrahydrofuran was charged to a 100 milliliter Parr reactor. Butadiene (3 milliliters) was charged to the reactor as a liquid under pressure. The reaction was heated to 95° C. and pressurized to 400 psig with 1:1 carbon monoxide:hydrogen. After one hour of reaction the solution was analyzed by gas chromatography to determine product composition. Butadiene was approximately 50% by weight converted. The products consisted of 28% by weight 3-pentenals, 36% by weight 4-pentenal, 7% by weight 2-pentenals, 8% by weight valeraldehyde, and 21% by weight low molecular weight products, possibly butenes.

EXAMPLE 19

A catalyst solution consisting of 0.05 grams of (bicyclo (2.2.1]hepta-2,5-diene) [1,1'-bis(diphenylphosphino) ferrocene] rhodium(I)perchlorate (250 parts per million rhodium) in 25 milliliters of tetrahydrofuran was charged to a 100 milliliter Parr reactor. Butadiene (3 milliliters) was charged to the reactor as a liquid under pressure. The reaction was heated to 95° C. and pressurized to 500 psig with 10:1 carbon monoxide:hydrogen. After one hour of reaction the solution was analyzed by gas chromatography to determine product composition. Butadiene was approximately 25% by weight converted. The products consisted of 17% by weight 3-pentenals, 34% by weight 4-pentenal, and 43% by weight low molecular weight products, possibly butenes.

EXAMPLE 20

A catalyst solution consisting of 0.02 grams of bis(bicyclo [2.2.1]hepta-2,5-diene)rhodium(I)perchlorate/bis-(diphenylphosphino)ferrocene (250 parts per million rhodium) and 0.03 grams of bis(diphenylphosphino) ferrocene in 25 milliliters of tetrahydrofuran was charged to a 100 milliliter Parr reactor. Butadiene (3 milliliters) was charged to the reactor as a liquid under pressure. The reaction was heated to 95° C. and pressurized to 500 psig with 1:1 carbon monoxide:hydrogen. After 30 minutes of reaction the solution was analyzed by gas chromatography to determine product composition. Butadiene conversion was undetermined. The products consisted of 38% by weight 3-pentenals, 43% by weight 4-pentenal, and 20% by weight low molecular weight products, possibly butenes.

EXAMPLE 21

A catalyst solution consisting of 0.018 grams of rhodium dicarbonyl acetylacetonate (300 parts per million rhodium), 0.035 grams of (4R,5R)-(-)—O-isopropylidene-2,3-dihydroxy-1,4-bis(diphenylphosphino)butane ligand (1:1 ligand to rhodium ratio), and 25 milliliters of tetrahydrofuran was charged to a 100 milliliter Parr reactor. Butadiene (3 milliliters) was charged to the reactor as a liquid under pressure. The reaction was heated to 95° C. and pressurized to 250 psig with 4:1 carbon monoxide:hydrogen. After thirty minutes of reaction the solution was analyzed by gas chromatography to determine product composition. The products consisted of 57% by weight 3-pentenals, and 32% by weight 4-pentenal. After 2 hours of reaction, butadiene was approximately 83% by weight converted. The products consisted of 53% by weight 3-pentenals, 8% by weight 4-pentenal, 3% by weight valeraldehyde, 6% by weight branched dialdehydes, and 22% by weight adipaldehyde.

EXAMPLE 22

A catalyst solution consisting of 0.018 grams of rhodium dicarbonyl acetylacetonate (300 parts per million rhodium), 0.35 grams of (4R,5R)-(-)-O-isopropylidene-2,3-dihydroxy-1,4-bis(diphenylphosphino)butane ligand (10:1 ligand to rhodium ratio), and 25 milliliters of tetrahydrofuran was charged to a 100 milliliter Parr reactor. Butadiene (3 milliliters) was charged to the reactor as a liquid under pressure. The reaction was heated to 95° C. and pressurized to 500 psig with 1:1 carbon monoxide:hydrogen. After 2 hours of reaction, the solution was analyzed by gas chromatography to determine product composition. Butadiene was greater than 90% by weight converted. The products consisted of 41% by weight 3-pentenals, 3% by weight 2-pentenals, 8% by weight valeraldehyde, 10% by weight branched dialdehydes, and 24% by weight adipaldehyde.

EXAMPLE 23

A catalyst solution consisting of 0.003 grams of rhodium dicarbonyl acetylacetonate (50 parts per million rhodium), 0.039 grams of Ligand D (5:1 ligand to rhodium ratio), and 25 milliliters of tetrahydrofuran was charged to a 100 milliliter Parr reactor. 4-Pentenal (1 milliliter) was charged to the reactor and the reaction was heated to 60° C. and pressurized to 80 psig with 1:1 carbon monoxide:hydrogen. After 1 hour of reaction the solution was analyzed by gas chromatography to determine product composition. 4-Pentenal was approximately 93% by weight converted. The products consisted of 80% by weight adipaldehyde, 4% valeraldehyde, less than 1% methylglutaraldehyde, and 14% by weight 3-pentenals.

EXAMPLE 24

A catalyst solution consisting of 0.003 grams of rhodium dicarbonyl acetylacetonate (50 parts per million rhodium), 0.044 grams of Ligand D (5:1 ligand to rhodium ratio), and 25 milliliters of tetrahydrofuran was charged to a 100 milliliter Parr reactor. 4-Pentenal (1 milliliter) was charged to the reactor and the reaction was heated to 75° C. and pressurized to 200 psig with 1:3 carbon monoxide:hydrogen. After two hours of reaction the solution was analyzed by gas chromatography to determine product composition. 4-Pentenal was completely converted. The products consisted of 76% by weight adipaldehyde, 2% methylglutaraldehyde, 4% 3-pentenals and 15% by weight valeraldehyde.

EXAMPLE 25

A catalyst solution consisting of 0.003 grams of rhodium dicarbonyl acetylacetonate (50 parts per million rhodium), 0.006 grams of 9,9-dimethyl-4,6-bis(diphenylphosphino) xanthene (1:1 ligand to rhodium ratio), and 25 milliliters of tetrahydrofuran was charged to a 100 milliliter Parr reactor. 4-Pentenal (1 milliliter) was charged to the reactor and the reaction was heated to 75° C. and pressurized to 100 psig with 1:1 carbon monoxide:hydrogen. After two hours of reaction the solution was analyzed by gas chromatography to determine product composition. 4-Pentenal was 26% by weight converted. The products consisted of 83% by weight adipaldehyde, 10% methylglutaraldehyde, and 7% 3-pentenals.

EXAMPLE 26

A catalyst solution consisting of 0.018 grams of rhodium dicarbonyl acetylacetonate (300 parts per million rhodium), 0.04 grams of bis(diphenylphosphino)ruthenocene (1:1 ligand to rhodium ratio), and 25 milliliters of tetrahydrofuran was charged to a 100 milliliter Parr reactor. 4-Pentenal (1 milliliter) was charged to the reactor and the reaction was heated to 75° C. and pressurized to 100 psig with 1:1 carbon monoxide:hydrogen. After two hours of reaction the solution was analyzed by gas chromatography to determine product composition. 4-Pentenal was completely converted. The products consisted of 71% by weight adipaldehyde, 21% methylglutaraldehyde, and 3% 3-pentenals.

EXAMPLE 27

A catalyst solution consisting of 0.003 grams of rhodium dicarbonyl acetylacetonate (50 parts per million rhodium), 0.05 grams of Ligand D (5:1 ligand to rhodium ratio), 0.496 grams of diglyme (as an internal standard) and 25 milliliters of tetrahydrofuran was charged to a 100 milliliter Parr reactor. 4-Pentenal (0.5 milliliters) was charged to the reactor and the reaction was heated to 85° C. and pressurized to 190 psig with 1:1 carbon monoxide:hydrogen. After 1 hour of reaction the solution was analyzed by gas chromatography to determine product composition. The products consisted of 88.3% by weight adipaldehyde, 6.4% valeraldehyde and 5.2% by weight 3-pentenals.

EXAMPLE 28

Caprolactone was shown to be produced from adipaldehyde. Stock solutions of freshly distilled adipaldehyde in toluene and hexadecane (internal standard) and bis (triphenylphosphine)rhodium allyl, [Rh(C$_3$H$_5$)(PPh$_3$)$_2$], in toluene were prepared. A calculated amount of each stock solution (see millimoles of charge for each vial in Table B below) was added to each of 3 reaction tubes which had previously been evacuated and filled with nitrogen 3 times. Dry toluene was added to each vial to bring the total volume to 2 milliliters, then the vials were purged with hydrogen for 20 minutes. After this time, the vials were capped and allowed to stir overnight. Gas chromatographic analysis was done on a HP 5890 gas chromatograph equipped with a DB1 column. Adipaldehyde was not detected in the reaction mixture in any of the vials at the conclusion of the reaction. The results are given in Table B.

TABLE B

|  | initial mmol Adip. | Initial mmol TPP$_2$(Rh)allyl | mmol Capro. produced | Selectivity |
|---|---|---|---|---|
| Vial 1 | 0.107 | 0.065 | 0.033 | 31% |
| Vial 2 | 0.214 | 0.065 | 0.058 | 27% |
| Vial 3 | 1.070 | 0.065 | 0.059 | 6% |

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process for selectively producing one or more substituted or unsubstituted 1,6-hexanedials which comprises:
    (a) subjecting one or more substituted or unsubstituted alkadienes or a mixture comprising one or more substituted or unsubstituted alkadienes to hydroformylation in the presence of a hydroformylation catalyst and at an alkadiene partial pressure and/or a carbon monoxide partial pressure sufficient to selectively produce one or more substituted or unsubstituted pentenals or a reaction mixture comprising one or more substituted or unsubstituted pentenals and to prevent or minimize derivatization of substituted or unsubstituted 3-potentenals, wherein the amount of 4-pentenals produced in step (a) is at least about 10% by weight; and
    (b) subjecting said one or more substituted or unsubstituted pentenals or said reaction mixture comprising one or more substituted or unsubstituted pentenals to hydroformylation in the presence of a hydroformylation catalyst to selectively produce said one or more substituted or unsubstituted 1,6-hexanedials.

2. A process for selectively producing one or more substituted or unsubstituted 1,6-hexanedials which comprises:
    (a) reacting one or more substituted or unsubstituted alkadienes or a mixture comprising one or more substituted or unsubstituted alkadienes with hydrogen and carbon monoxide in the presence of a catalytic amount of a metal-ligand complex catalyst and at an alkadiene partial pressure and/or a carbon monoxide partial pressure sufficient to selectively produce one or more substituted or unsubstituted pentenals or a reaction mixture comprising one or more substituted or unsubstituted pentenals and to prevent or minimize derivatization of substituted or unsubstituted 3-pentenals, wherein the amount of 4-pentenals produced in step (a) is at least about 10% by weight; and (b) reacting said one or more substituted or unsubstituted pentenals or said reaction mixture comprising one or more substituted or unsubstituted pentenals with hydrogen and carbon monoxide in the presence of a catalytic amount of a metal-ligand complex catalyst to selectively produce said one or more substituted or unsubstituted 1,6-hexanedials.

3. The process of claim 1 wherein the substituted or unsubstituted alkadiene comprises butadiene and the substituted or unsubstituted 1,6-hexanedial comprises adipaldehyde.

4. The process of claim 1 wherein the hydroformylation conditions in steps (a) and (b) are the same or different and the hydroformylation catalysts in steps (a) and (b) are the same or different.

5. The process of claim 2 wherein said metal-ligand complex catalyst comprises a metal selected from a Group 8, 9 and 10 metal complexed with an organophosphorus ligand selected from a mono-, di-, tri- and polyorganophosphine ligand.

6. The process of claim 2 wherein said metal-ligand complex catalyst comprises a metal selected from a Group 8, 9 and 10 metal complexed with an organophosphorus ligand selected from:

(i) a triorganophosphine ligand represented by the formula:

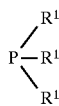

wherein each $R^1$ is the same or different and is a substituted or unsubstituted monovalent hydrocarbon radical;

(ii) a monoorganophosphite represented by the formula:

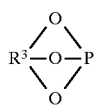

wherein $R^3$ represents a substituted or unsubstituted trivalent hydrocarbon radical containing from 4 to 40 carbon atoms or greater;

(iii) a diorganophosphite represented by the formula:

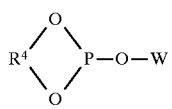

wherein $R^4$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater;

(iv) a triorganophosphite represented by the formula:

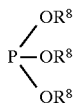

wherein each $R^8$ is the same or different and is a substituted or unsubstituted monovalent hydrocarbon radical; and (v) an organopolyphosphite containing two or more tertiary (trivalent) phosphorus atoms represented by the formula:

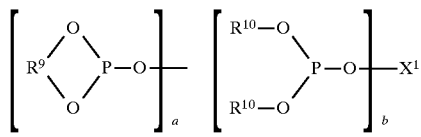

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b.

7. The process of claim 2 wherein said metal-ligand complex catalyst comprises a metal selected from a Group 8, 9 and 10 metal complexed with an organophosphorus ligand having the formula:

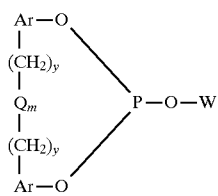

wherein W represents a substituted or unsubstituted monovalent hydrocarbon radical containing from 1 to 18 carbon atoms or greater, each Ar is the same or different and represents a substituted or unsubstituted aryl radical, each y is the same or different and is a value of 0 or 1, Q represents a divalent bridging group selected from —C($R^5$)$_2$—, —O—, —S—, —NR$^6$—, Si($R^7$)$_2$— and —CO—, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1.

8. The process of claim 2 wherein said metal-ligand complex catalyst comprises a metal selected from a Group 8, 9 and 10 metal complexed with an organophosphorus ligand having the formula selected from:

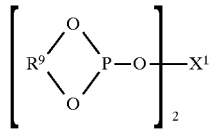

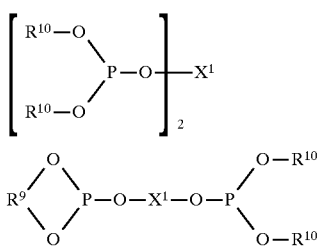

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, and each $R^{10}$ is the same or different and is a substituted or unsubstituted monovalent hydrocarbon radical containing from 1 to 24 carbon atoms.

9. The process of claim 2 wherein said metal-ligand complex catalyst comprises a metal selected from a Group 8, 9 and 10 metal complexed with an organophosphorus ligand having the formula selected from:

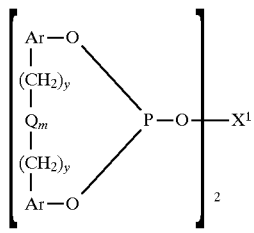

wherein $X^1$ represents a substituted or unsubstituted n-valent hydrocarbon bridging radical containing from 2 to 40 carbon atoms, each $R^9$ is the same or different and is a divalent hydrocarbon radical containing from 4 to 40 carbon atoms, each $R^{10}$ is the same or different and is a substituted or unsubstituted monovalent hydrocarbon radical containing from 1 to 24 carbon atoms, each Ar is the same or different and represents a substituted or unsubstituted aryl radical, each y is the same or different and is a value of 0 or 1, Q represents a divalent bridging group selected from $-C(R^5)_2-$, $-O-$, $-S-$, $-NR^{6-}$, $Si(R^7)_2-$ and $-CO-$, wherein each $R^5$ is the same or different and represents hydrogen, alkyl radicals having from 1 to 12 carbon atoms, phenyl, tolyl, and anisyl, $R^6$ represents hydrogen or a methyl radical, each $R^7$ is the same or different and represents hydrogen or a methyl radical, and m is a value of 0 or 1.

10. The process of claim 1 which is conducted at a temperature from about 20° C. to 200° C. and at a total pressure from about 20 psig to about 3000 psig.

11. A process for producing a batchwise or continuously generated reaction mixture comprising:
   (1) one or more substituted or unsubstituted 1,6-hexanedials;
   (2) one or more substituted or unsubstituted pentenals;
   (3) one or more substituted 1,5-pentanedials;
   (4) one or more substituted 1,4-butanedials;
   (5) optionally valeraldehyde; and
   (6) one or more substituted or unsubstituted alkadienes;
wherein the weight ratio of component (1) to component (2) is greater than about 0.01; the weight ratio of component (1) to the sum of components (2), (3), (4) and (5) is greater than about 0.1; and the weight ratio of component (6) to the sum of components (1), (2), (3), (4) and (5) is about 0 to about 100;

which process comprises: (a) reacting one or more substituted or unsubstituted alkadienes or a mixture comprising one or more substituted or unsubstituted alkadienes with hydrogen and carbon monoxide in the presence of a catalytic amount of a metal-ligand complex catalyst and at an alkadiene partial pressure and/or a carbon monoxide partial pressure sufficient to selectively produce one or more substituted or unsubstituted pentenals or a reaction mixture comprising one or more substituted or unsubstituted pentenals and to prevent or minimize derivatization of substituted or unsubstituted 3-pentenals, wherein the amount of 4-pentenals produced in step (a) is at least about 10% by weight; and (b) reacting said one or more substituted or unsubstituted pentenals or said reaction mixture comprising one or more substituted or unsubstituted pentenals with hydrogen and carbon monoxide in the presence of a catalytic amount of a metal-ligand complex catalyst to produce said batchwise or continuously generated reaction mixture.

12. The process of claim 11 wherein the hydroformylation conditions in steps (a) and (b) are the same or different and the hydroformylation catalysts in steps (a) and (b) are the same or different.

13. A process for producing a reaction mixture comprising one or more substituted or unsubstituted 1,6-hexanedials which process comprises: (a) reacting one or more substituted or unsubstituted alkadienes or a mixture comprising one or more substituted or unsubstituted alkadienes with hydrogen and carbon monoxide in the presence of a catalytic amount of a metal-ligand complex catalyst and at an alkadiene partial pressure and/or a carbon monoxide partial pressure sufficient to selectively produce one or more substituted or unsubstituted pentenals or a reaction mixture comprising one or more substituted or unsubstituted pentenals and to prevent or minimize derivatization of substituted or unsubstituted 3-pentenals, wherein the amount of 4-pentenals produced in step (a) is at least about 10% by weight; and (b) reacting said one or more substituted or unsubstituted pentenals or said reaction mixture comprising one or more substituted or unsubstituted pentenals with hydrogen and carbon monoxide in the presence of a catalytic amount of a metal-ligand complex catalyst to produce said reaction mixture comprising one or more substituted or unsubstituted 1,6-hexanedials.

14. The process of claim 13 wherein the hydroformylation conditions in steps (a) and (b) are the same or different and the hydroformylation catalysts in steps (a) and (b) are the same or different.

15. A process for producing one or more substituted or unsubstituted 1,6-hexanedials which comprises:
   (a) subjecting one or more substituted or unsubstituted alkadienes or a mixture comprising one or more substituted or unsubstituted alkadienes to hydroformylation in the presence of a hydroformylation catalyst and at an alkadiene partial pressure and/or a carbon monoxide partial pressure sufficient to produce one or more substituted or unsubstituted unsaturated aldehydes comprising 3-pentenals and/or 4-pentenal and to prevent or minimize derivatization of substituted or unsubstituted 3-pentenals, wherein the amount of 4-pentenals produced in step (a) is at least about 10% by weight;
   (b) optionally separating the 3-pentenals and/or 4-pentenal from the hydroformylation catalyst before any substantial amount of 2-pentenals form; and
   (c) subjecting said one or more substituted or unsubstituted unsaturated aldehydes comprising 3-pentenals and/or 4-pentenal to hydroformylation in the presence of a hydroformylation catalyst to produce said one or more substituted or unsubstituted 1,6-hexanedials.

16. The process of claim 15 wherein the hydroformylation conditions in steps (a) and (c) are the same or different and the hydroformylation catalysts in steps (a) and (c) are the same or different.

17. A process for producing one or more substituted or unsubstituted 1,6-hexanedials which comprises:
(a) subjecting one or more substituted or unsubstituted alkadienes or a mixture comprising one or more substituted or unsubstituted alkadienes to hydroformylation in the presence of a hydroformylation catalyst and at an alkadiene partial pressure and/or carbon monoxide partial pressure sufficient to produce one or more substituted or unsubstituted unsaturated aldehydes comprising 2-pentenals, 3-pentenals and/or 4-pentenal and to prevent or minimize derivatization of substituted or unsubstituted 3-pentenals, wherein the amount of 4-pentenals produced in step (a) is at least about 10% by weight;
(b) optionally separating the 2-pentenals, 3-pentenals and/or 4-pentenal from the hydroformylation catalyst; and
(c) subjecting said one or more substituted or unsubstituted unsaturated aldehydes comprising 2-pentenals, 3-pentenals and/or 4-pentenal to hydroformylation in the presence of a hydroformylation catalyst to produce said one or more substituted or unsubstituted 1,6-hexanedials.

18. The process of claim 17 wherein the hydroformylation conditions in steps (a) and (c) are the same or different and the hydroformylation catalysts in steps (a) and (c) are the same or different.

19. A process for producing one or more substituted or unsubstituted 1,6-hexanedials which comprises:
(a) subjecting one or more substituted or unsubstituted alkadienes or a mixture comprising one or more substituted or unsubstituted alkadienes to hydroformylation in the presence of a hydroformylation catalyst and at an alkadiene partial pressure and/or a carbon monoxide partial pressure sufficient to produce one or more unsaturated aldehydes comprising 3-pentenals and/or 4-pentenal and to prevent or minimize derivatization of substituted or unsubstituted 3-pentenals, wherein the amount of 4-pentenals produced in step (a) is at least about 10% by weight;
(b) optionally separating the 3-pentenals and/or 4-pentenal from the hydroformylation catalyst before any substantial amount of 2-pentenals form;
(c) optionally subjecting the 3-pentenals and/or 4-pentenal to isomerization in the presence of a heterogeneous or homogeneous olefin isomerization catalyst to partially or completely isomerize the 3-pentenals to 4-pentenal; and
(d) subjecting said one or more substituted or unsubstituted unsaturated aldehydes comprising 3-pentenals and/or 4-pentenal to hydroformylation in the presence of a hydroformylation catalyst to produce said one or more substituted or unsubstituted 1,6-hexanedials.

20. The process of claim 19 wherein the hydroformylation conditions in steps (a) and (d) are the same or different and the hydroformylation catalysts in steps (a) and (d) are the same or different.

21. A process for producing one or more substituted or unsubstituted 1,6-hexanedials which comprises:
(a) subjecting one or more substituted or unsubstituted alkadienes or a mixture comprising one or more substituted or unsubstituted alkadienes to hydroformylation in the presence of a hydroformylation catalyst and at an alkadiene partial pressure and/or a carbon monoxide partial pressure sufficient to produce one or more substituted or unsubstituted unsaturated aldehydes comprising 2-pentenals, 3-pentenals and/or 4-pentenal and to prevent or minimize derivatization of substituted or unsubstituted 3-pentenals, wherein the amount of 4-pentenals produced in step (a) is at least about 10% by weight;
(b) optionally separating the 2-pentenals, 3-pentenals and/or 4-pentenal from the hydroformylation catalyst;
(c) optionally subjecting the 2-pentenals, 3-pentenals and/or 4-pentenal to isomerization in the presence of a heterogeneous or homogeneous olefin isomerization catalyst to partially or completely isomerize the 2-pentenals and/or 3-pentenals to 3-pentenals and/or 4-pentenal; and
(d) subjecting said one or more substituted or unsubstituted unsaturated aldehydes comprising 2-pentenals, 3-pentenals and/or 4-pentenal to hydroformylation in the presence of a hydroformylation catalyst to produce said one or more substituted or unsubstituted 1,6-hexanedials.

22. The process of claim 21 wherein the hydroformylation conditions in steps (a) and (d) are the same or different and the hydroformylation catalysts in steps (a) and (d) are the same or different.

23. A process for producing one or more substituted or unsubstituted 1,6-hexanedials which comprises:
(a) subjecting one or more substituted or unsubstituted alkadienes or a mixture comprising one or more substituted or unsubstituted alkadienes to hydroformylation in the presence of a hydroformylation catalyst and at an alkadiene partial pressure and/or a carbon monoxide partial pressure sufficient to produce one or more substituted or unsubstituted unsaturated aldehydes comprising 3-pentenals and/or 4-pentenal and to prevent or minimize derivatization of substituted or unsubstituted 3-pentenals, wherein the amount of 4-pentenals produced in step (a) is at least about 10% by weight;
(b) optionally separating the 3-pentenals and/or 4-pentenal from the hydroformylation catalyst before any substantial amount of 2-pentenals form;
(c) subjecting the 3-pentenals and/or 4-pentenal to acetalization optionally in the presence of an acetalization catalyst to produce one or more substituted or unsubstituted acetals of 3-pentenals and water;
(d) optionally separating said one or more substituted or unsubstituted acetals of 3-pentenals and/or 4-pentenal from the water;
(e) subjecting said one or more substituted or unsubstituted acetals of 3-pentenals and/or 4-pentenal to hydroformylation in the presence of a hydroformylation catalyst to produce one or more substituted or unsubstituted monoacetals of 1,6-hexanedial; and
(f) subjecting said one or more substituted or unsubstituted monoacetals of 1,6-hexanedial to hydrolysis in the presence of a hydrolysis catalyst to produce said one or more substituted or unsubstituted 1,6-hexanedials.

24. The process of claim 23 wherein the hydroformylation conditions in steps (a) and (e) are the same or different and the hydroformylation catalysts in steps (a) and (e) are the same or different.

25. A process for producing one or more substituted or unsubstituted 1,6-hexanedials which comprises:

(a) subjecting one or more substituted or unsubstituted alkadienes or a mixture comprising one or more substituted or unsubstituted alkadienes to hydroformylation in the presence of a hydroformylation catalyst and at an alkadiene partial pressure and/or a carbon monoxide partial pressure sufficient to produce one or more unsaturated aldehydes comprising 2-pentenals, 3-pentenals and/or 4-pentenal and to prevent or minimize derivatization of substituted or unsubstituted 3-pentenals, wherein the amount of 4-pentenals produced in step (a) is at least about 10% by weight;

(b) optionally separating the 2-pentenals, 3-pentenals and/or 4-pentenal from the hydroformylation catalyst;

(c) subjecting the 2-pentenals, 3-pentenals and/or 4-pentenal to acetalization optionally in the presence of an acetalization catalyst to produce one or more substituted or unsubstituted acetals of 3-pentenals and water;

(d) optionally separating said one or more substituted or unsubstituted acetals of 2-pentenals, 3-pentenals and/or 4-pentenal from the water;

(e) subjecting said one or more substituted or unsubstituted acetals of 2-pentenals, 3-pentenals and/or 4-pentenal to hydroformylation in the presence of a hydroformylation catalyst to produce one or more substituted or unsubstituted monoacetals of 1,6-hexanedial; and (f) subjecting said one or more substituted or unsubstituted monoacetals of 1,6-hexanedial to hydrolysis in the presence of a hydrolysis catalyst to produce said one or more substituted or unsubstituted 1,6-hexanedials.

26. The process of claim 25 wherein the hydroformylation conditions in steps (a) and (e) are the same or different and the hydroformylation catalysts in steps (a) and (e) are the same or different.

27. A batchwise or continuously generated reaction mixture comprising:

(1) one or more substituted or unsubstituted 1,6-hexanedials;

(2) one or more substituted or unsubstituted pentenals;

(3) one or more substituted 1,5-pentanedials;

(4) one or more substituted 1,4-butanedials;

(5) optionally valeraldehyde; and (6) one or more substituted or unsubstituted alkadienes; wherein the weight ratio of component (1) to component (2) is greater than about 0.01; the weight ratio of component (1) to the sum of components (2), (3), (4) and (5) is greater than about 0.1; and the weight ratio of component (6) to the sum of components (1), (2), (3), (4) and (5) is about 0 to about 100.

28. A reaction mixture comprising one or more substituted or unsubstituted 1,6-hexanedials in which said reaction mixture is prepared by a process which comprises: (a) reacting one or more substituted or unsubstituted alkadienes or a mixture comprising one or more substituted or unsubstituted alkadienes with hydrogen and carbon monoxide in the presence of a catalytic amount of a metal-ligand complex catalyst and at an alkadiene partial pressure and/or a carbon monoxide partial pressure sufficient to selectively produce one or more substituted or unsubstituted pentenals or a reaction mixture comprising one or more pentenals and to prevent or minimize derivatization of substituted or unsubstituted 3-pentenals, wherein the amount of 4-pentenals produced in step (a) is at least about 10% by weight; and (b) reacting said one or more substituted or unsubstituted pentenals or said reaction mixture comprising one or more substituted or unsubstituted pentenals with hydrogen and carbon monoxide in the presence of a catalytic amount of a metal-ligand complex catalyst to produce said reaction mixture comprising one or more substituted or unsubstituted 1,6-hexanedials.

29. The reaction mixture of claim 28 wherein the hydroformylation conditions in steps (a) and (b) are the same or different and the hydroformylation catalysts in steps (a) and (b) are the same or different.

30. The reaction mixture of claim 28 in which the process further comprises derivatizing the one or more substituted or unsubstituted 1,6-hexanedials.

31. The reaction mixture of claim 30 in which the derivatizing reaction comprises hydrogenation, hydroformylation, esterification, etherification, amination, cyclization, acetalization, alkylation, dehydrogenation, reduction, acylation, condensation, oxidation, silylation and permissible combinations thereof.

* * * * *